United States Patent
Schwalm et al.

(10) Patent No.: US 11,351,742 B2
(45) Date of Patent: *Jun. 7, 2022

(54) METHOD AND DEVICE FOR THE STERILE CONNECTION OF PIPES

(71) Applicant: Fresenius Kabi Deutschland GmbH, Bad Homburg (DE)

(72) Inventors: Michael Schwalm, Alsfeld (DE); Thomas Brückner, Mombris (DE)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 201 days.

This patent is subject to a terminal disclaimer.

(21) Appl. No.: 16/728,201

(22) Filed: Dec. 27, 2019

(65) Prior Publication Data

US 2020/0130290 A1    Apr. 30, 2020

Related U.S. Application Data

(60) Continuation of application No. 16/208,931, filed on Dec. 4, 2018, now Pat. No. 10,549,484, which is a
(Continued)

(30) Foreign Application Priority Data

Aug. 18, 2010  (EP) ..................... 10173187

(51) Int. Cl.
*A61M 25/00* (2006.01)
*B29C 65/00* (2006.01)
(Continued)

(52) U.S. Cl.
CPC ....... *B29C 66/1142* (2013.01); *A61M 39/146* (2013.01); *B29C 65/04* (2013.01); *B29C 65/743* (2013.01); *B29C 65/7802* (2013.01); *B29C 65/7841* (2013.01); *B29C 66/0224* (2013.01); *B29C 66/5221* (2013.01);
(Continued)

(58) Field of Classification Search
CPC .. B65D 83/425; B65D 83/205; B65D 83/682; B65D 83/7532; B65B 3/12; B65B 31/003
See application file for complete search history.

(56) References Cited

U.S. PATENT DOCUMENTS

| 4,610,670 A | 9/1986 | Spencer |
| 4,619,642 A | 10/1986 | Spencer |

(Continued)

FOREIGN PATENT DOCUMENTS

| EP | 0208004 B1 | 8/1988 |
| EP | 0134630 B1 | 5/1989 |

(Continued)

OTHER PUBLICATIONS

European Patent Office, European Search Report, counterpart EP18167652, dated Aug. 9, 2018 with computer generated English translation.

*Primary Examiner* — P. Macade Nichols
(74) *Attorney, Agent, or Firm* — Cook Alex Ltd.

(57) ABSTRACT

A method is described for opening a heat bonded sterile connection that includes a skin of material blocking flow between the connection site. The method includes applying external pressure to the connection site.

20 Claims, 21 Drawing Sheets

1a

1b

Related U.S. Application Data continuation of application No. 15/465,915, filed on Mar. 22, 2017, now Pat. No. 10,569,478, which is a division of application No. 13/812,988, filed as application No. PCT/EP2011/063541 on Aug. 5, 2011, now Pat. No. 10,040,247.

(60) Provisional application No. 61/374,640, filed on Aug. 18, 2010.

(51) Int. Cl.

| | | |
|---|---|---|
| *A61M 39/14* | (2006.01) | |
| *B29C 65/04* | (2006.01) | |
| *B29C 65/74* | (2006.01) | |
| *B29C 65/78* | (2006.01) | |
| *F16L 55/00* | (2006.01) | |
| *B29K 27/06* | (2006.01) | |

(52) U.S. Cl.
CPC .... *B29C 66/81431* (2013.01); *B29C 66/8221* (2013.01); *B29C 66/8324* (2013.01); *B29C 66/8414* (2013.01); *B29C 66/8416* (2013.01); *B29C 66/857* (2013.01); *B29C 66/91211* (2013.01); *B29C 66/91221* (2013.01); *B29C 66/91651* (2013.01); *B29C 66/9221* (2013.01); *F16L 55/00* (2013.01); *B29C 66/71* (2013.01); *B29C 66/73921* (2013.01); *B29C 66/81871* (2013.01); *B29C 66/919* (2013.01); *B29K 2027/06* (2013.01); *Y10T 137/0402* (2015.04)

(56) References Cited

U.S. PATENT DOCUMENTS

| | | |
|---|---|---|
| 4,737,214 A | 4/1988 | Leurink et al. |
| 5,221,267 A | 6/1993 | Folden |
| 5,250,041 A | 10/1993 | Folden et al. |
| 5,256,229 A | 10/1993 | Spencer |
| 5,270,003 A | 12/1993 | Bernes et al. |
| 5,272,304 A | 12/1993 | Been et al. |
| 5,279,685 A | 1/1994 | Ivansons et al. |
| 5,836,619 A | 11/1998 | Shemesh et al. |
| 6,026,882 A | 2/2000 | Yamada et al. |
| 6,322,551 B1 | 11/2001 | Brugger |
| 6,485,593 B1 | 11/2002 | Christoffersen |
| 7,070,589 B2 | 7/2006 | Lolachi et al. |
| 7,766,394 B2 | 8/2010 | Sage et al. |
| 8,146,642 B2 | 4/2012 | Landherr et al. |
| 9,533,135 B2 | 1/2017 | Kusters et al. |
| 10,549,484 B2 * | 2/2020 | Schwalm ............ B29C 66/5221 |
| 2007/0182055 A1 | 8/2007 | Eells et al. |
| 2007/0296890 A1 | 12/2007 | Mizushima et al. |
| 2011/0144581 A1 | 6/2011 | Irwin et al. |
| 2012/0226229 A1 | 9/2012 | Watanabe et al. |
| 2013/0153048 A1 | 6/2013 | Schwalm et al. |
| 2016/0361531 A1 | 12/2016 | Kusters et al. |

FOREIGN PATENT DOCUMENTS

| | | |
|---|---|---|
| EP | 0194873 B1 | 7/1991 |
| EP | 0507321 | 10/1992 |
| EP | 0515811 A2 | 12/1992 |
| EP | 0723851 A2 | 7/1996 |
| EP | 0728274 A1 | 8/1996 |
| EP | 0847847 A1 | 6/1998 |
| EP | 0599057 B1 | 12/1999 |
| EP | 0623032 B1 | 8/2001 |
| EP | 1066853 B1 | 9/2004 |
| EP | 1108444 B1 | 4/2014 |
| EP | 2957402 A1 | 12/2015 |
| EP | 2089094 B1 | 1/2016 |
| JP | H09206383 | 8/1997 |
| JP | 11178891 A | 7/1999 |
| WO | WO1994/012224 | 6/1994 |
| WO | WO99/64837 A1 | 12/1999 |
| WO | WO03/041746 A2 | 5/2003 |
| WO | WO2008/054699 | 5/2008 |
| WO | WO2011/144561 | 11/2011 |
| WO | WO2012/022635 | 2/2012 |
| WO | WO2013/004322 | 1/2013 |

\* cited by examiner

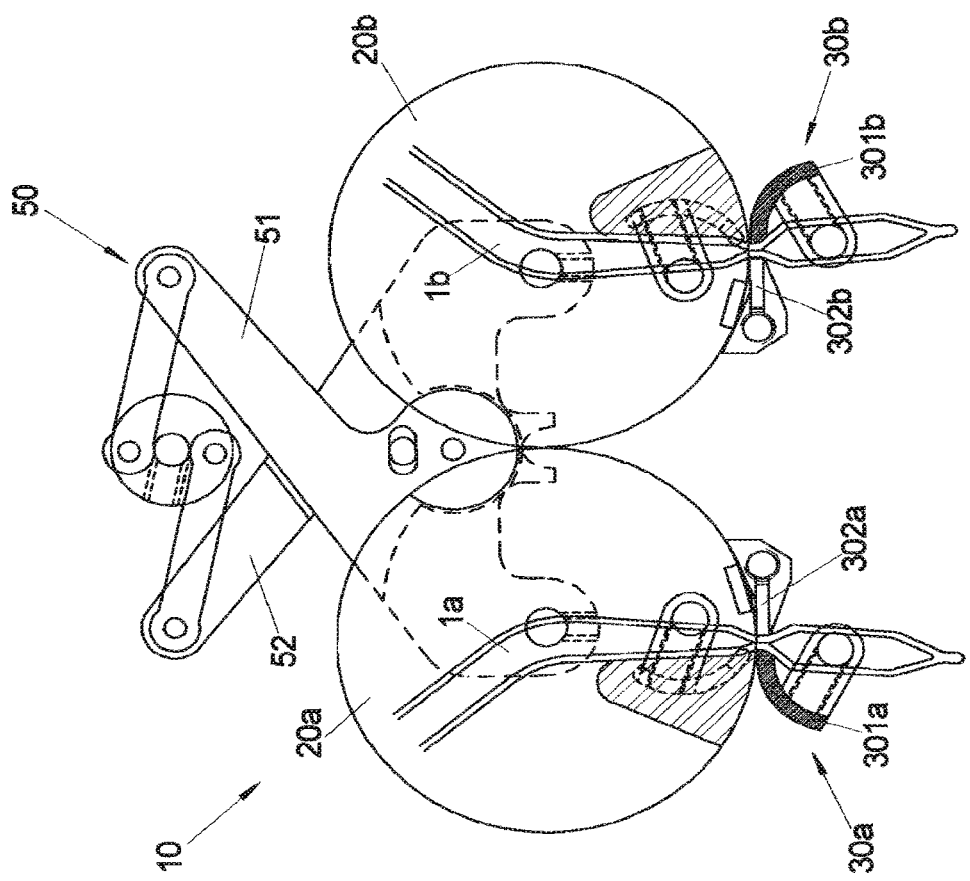
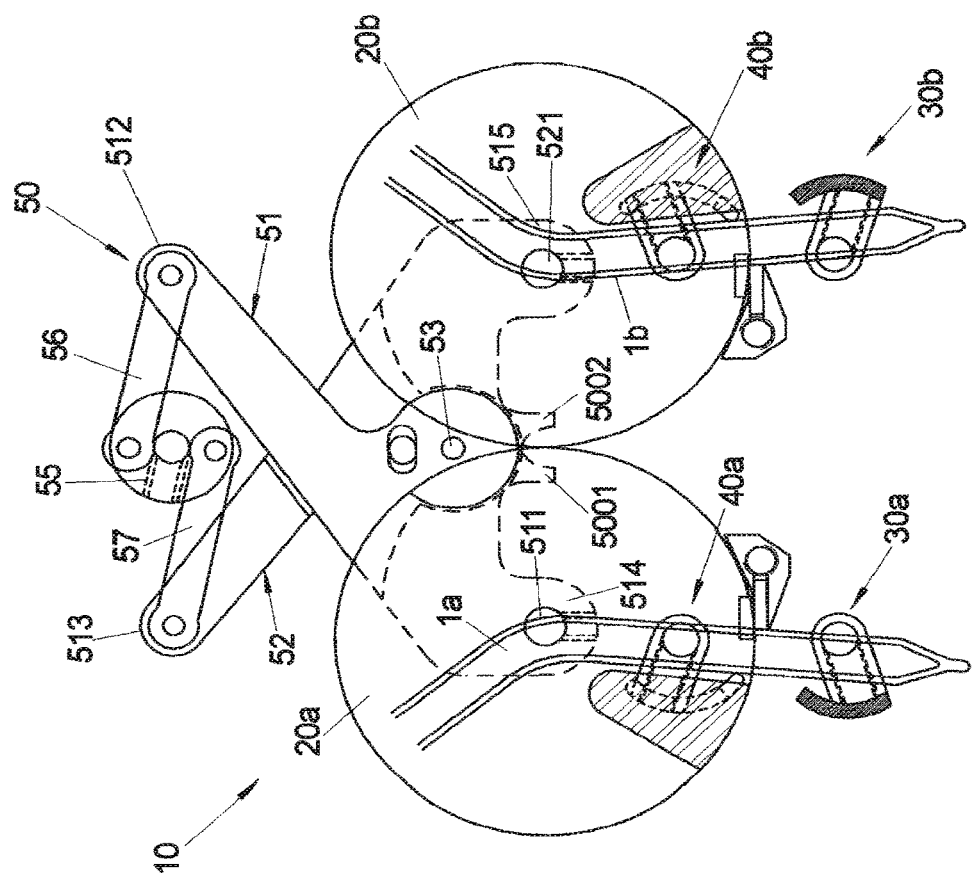

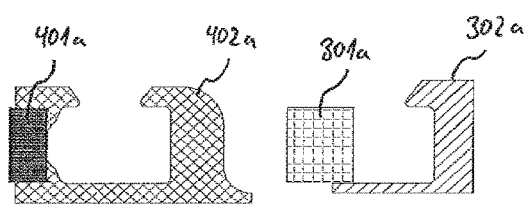
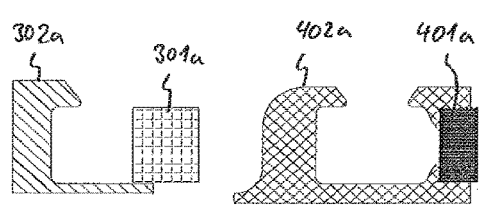
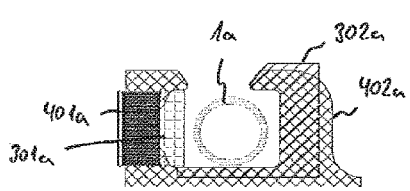
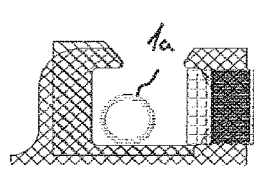
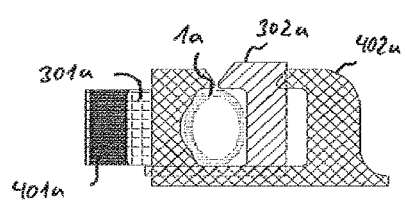
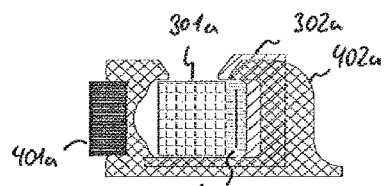
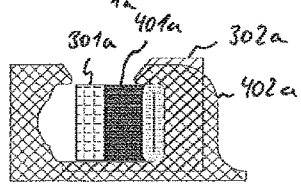
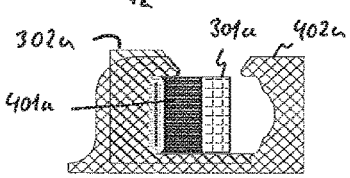
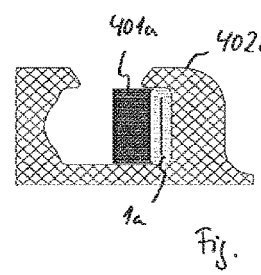
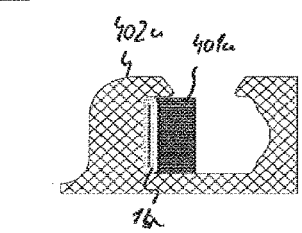

METHOD AND DEVICE FOR THE STERILE CONNECTION OF PIPES

CROSS REFERENCE TO RELATED APPLICATIONS

This application is a continuation of pending U.S. application Ser. No. 16/208,931, filed Dec. 4, 2018, which is a continuation of pending U.S. application Ser. No. 15/465,915, filed Mar. 22, 2017, which is a division of Ser. No. 13/812,988, filed Feb. 28, 2013, now U.S. Pat. No. 10,040,247, which is the U.S. national phase of international application no. PCT/EP2011/063541, filed Aug. 5, 2011, which claims priority to European application no. 10173187.5, filed Aug. 18, 2010, and U.S. provisional application No. 61/374,640, filed Aug. 18, 2010. The contents of the aforementioned applications are hereby incorporated by reference in their entirety.

The invention relates to a method for the connection of tubes according to claim 1 and to a device for the connection of tubes according to claim 7.

There is a need, in particular in the medical field, to be able to interconnect tubes in a sterile manner, said tubes being used for example for the transport of blood or infusion liquids. With a method, known from EP 1 555 111 A1, for the sterile connection of tubes, two tubes for example made of a thermoplastic material are first severed by means of a heated blade and two main portions of the severed tubes are interconnected by being moved toward one another along the heated blade and are pressed against one another once the blade has been removed. The blade has to be disposed of as hazardous waste after use.

The problem to be solved by the present invention lies in the provision of a method that enables the quickest possible connection of tubes and which generates minimal waste. The present invention is also based on the problem of creating a corresponding device for the connection of tubes.

The above problems are solved by the method having the features according to claim 1 and by the device having the features according to claim 7. Developments of the invention are disclosed in the dependant claims.

Accordingly, a method for the sterile connection of tubes is provided and comprises the following steps:
a) providing a first and a second tube;
b) heating a separating region of each of the first and second tubes using heating means;
c) mechanically separating the two tubes by exerting a tensile and/or shear force onto the tubes such that the two tubes are each separated in the heated separating region into a first and a second tube portion; and
d) producing mechanical contact, after separation of the tubes, between the end of the first tube portion of the first tube, formed by the separation of the first tube, and the end of the first tube portion of the second tube, formed by the separation of the second tube, wherein
e) the mechanical contact is produced such that the ends of the tube portions, as a result of the heating according to step b), still have such a temperature when they come into mechanical contact with one another that they form an integral bond with one another without additional heating after the separation process.

In accordance with the method according to the invention, a cutting tool therefore is not used to separate the two tubes, but the separation is achieved by heating a region (separating region) of the respective tube and introducing a tensile and/or shear force into the separating region softened by the heating. To exert a tensile force, the tubes are each held at one end in particular and a force is produced along a longitudinal axis, along which the tubes run at least in the separating region. A shear force (in particular acting in the respective separating region) may also be exerted onto each of the tubes, either at the same time or alternatively, wherein a force is generated for example and is generated perpendicularly or obliquely to the longitudinal axis of the tubes in the separating region.

For example, the tensile and/or shear force for separating the tubes is generated by a rotation and/or a translation of part of the respective tube. Possibilities for generating a tensile and/or shear force, which leads to the separation of the tubes in the heated separating region, will be explained in detail further below.

In accordance with the method according to the invention, there is preferably no separate heating of the ends of the first tube portions in addition to the heating according to step b) before said ends come into contact with one another. For example, the ends of the tube portions have a maximum temperature directly after the separation of the tubes and cool to a lower temperature until they come into contact with one another. This lower temperature is still high enough however that the two ends are integrally bonded together without further influence of heat. In particular, the mechanical contact between the ends of the first tube portions is produced so quickly that said ends, when they come into mechanical contact with one another, each still have a temperature that is greater than the melting point of the material of the respective tube portion. For example, the separating region of the tubes is heated (for example to above 200° C.), until the (thermoplastic) tube material reaches the thermoplastic state. The temperature of the ends of the first tube portions after separation of the tubes and until the connection thereof lies above 100° C. for example.

The ends of the first tube portions produced by the separation of the tubes can be sealed as a result of their lasting high temperature, such that a sterile closure of the first tube portions is produced in particular. Since the ends of the first tube portions have a temperature above the melting point of the tube material until their ends are interconnected, it is additionally ensured that this seal exists until the first tube portions are connected.

As already mentioned above, the two tubes are formed in particular from a thermoplastic material (for example from PVC or another plastic), wherein the two ends of the first tube portions are each still in their thermoplastic state when they come into contact with one another. It is not absolutely necessary however for the two tubes to consist of the same material, but tubes made of different materials, for example of different thermoplastics, can of course also be interconnected with the method according to the invention.

In accordance with one embodiment of the invention, the interval between the separation of the first and second tube and the moment of mechanical contact between the ends of the first tube portions is at most 0.1 s, in particular at most 0.05 s. The "moment of mechanical contact" is in particular the moment at which contact first occurs between the end of the first tube portion of the first tube and the end of the first tube portion of the second tube. In particular, the ends to be interconnected each have an end face, said end faces being pressed against one another to produce the mechanical contact, such that the moment at which the two end faces contact one another can also be considered as the "moment of mechanical contact".

It is noted that the invention naturally is not fixed to a specific interval between the separation of the tubes and the connection of the first tube portions. Much longer intervals than those disclosed above are also conceivable if the mechanical contact is produced sufficiently quickly to enable an integral bonding of the ends of the first tube portions without a further heating step. For example, the considered interval may be much greater than 0.1 s, and for example may be as much as one second.

The production of the mechanical contact between the ends of the two first tube portions in particular includes a step of moving the respective first tube portion (for example in the form of a main tube portion that is longer than the second tube portion) away from the respective second tube portion (for example in the form of an end of the original tube) and a step of moving the two first tube portions toward one another, aligning their ends along a common axis and pressing the two ends (in particular the end faces thereof) against one another.

For example, the step of moving the two first tube portions toward one another comprises a rotation of at least part of the first tube portion of the first tube and/or a rotation of at least part of the first tube portion of the second tube. Here, the two first tube portions (of the first and second tube) are mounted, for example on a respective receiving device, such that they can be moved toward one another as a result of rotation after separation of the first and second tube. Rotatable receiving devices of this type will be discussed in greater detail further below.

In particular, the first tube portion of the first tube and/or the first tube portion of the second tube is/are rotated about an axis of rotation that runs at least approximately perpendicularly to a plane along which the first tube portion extends at least in part. For example, the first tube portion of the first tube is mounted such that its end (which is to be connected to the end of the first tube region of the second tube) extends at least approximately in a straight line (that is to say along a longitudinal axis), wherein the axis of rotation is then oriented perpendicularly to this end running in a straight line. The wording stating that the tube portion extends "along a plane" therefore does not necessarily mean that it runs in a curved manner or with portions angled to one another. It is also possible that it extends substantially in a straight line, at least in part.

For example, a device for carrying out the above-described method is used and comprises the following:
a first receiving device for receiving a first tube;
a second receiving device for receiving a second tube;
heating means for heating a separating region of the first and second tube;
means for generating a tensile and/or shear force on the tubes so as to separate each of the two tubes in the heated separating region into a first and a second tube portion;
contact generation means for producing mechanical contact between the end of the first tube portion of the first tube, formed by the separation of the first tube, and the end of the first tube portion of the second tube, formed by the separation of the second tube, wherein
the contact generation means are designed to bring the ends of the tube portions, after separation of the tubes, into mechanical contact with one another so (quickly) that, as a result of the heating using the heating means, they still have such a temperature when they come into mechanical contact with one another that they form an integral bond with one another without renewed heating.

The invention also relates to a device for the sterile connection of tubes, in particular for carrying out a method as described above, comprising a first receiving device for receiving a first tube;
a second receiving device for receiving a second tube;
heating means for heating a separating region of a first tube arranged on the first receiving device and a separating region of a second tube arranged on the second receiving device; and
separating means for separating each of the first and second tubes in the heated separating region into a first and a second tube portion, wherein
the first and second receiving devices are each designed to hold the respective first tube portion such that it extends at least in part along a plane, and at least one of the two receiving devices is mounted rotatably about an axis of rotation that runs at least approximately perpendicularly to the plane, and wherein
the device is designed such that, after separation of the first and second tubes, an end of the first tube portion of the first tube can be brought into mechanical contact with an end of the first tube portion of the second tube with rotation of the first and/or second receiving device about the axis of rotation.

The contact between the ends of the first tube portions (and in particular the rotation of the first and/or the second receiving device) is produced in particular so quickly that the ends, as a result of the heating using the heating means, still have such a temperature when they come into mechanical contact with one another, even after the separation of the tubes (for example even once the heating means have been switched off), that they form an integral bond with one another without renewed heating, as described further above in reference to the method according to the invention.

To separate the tubes and to connect the first tube portions, a device of this type merely requires a single heat source (heating means), since there is no separate, additional heating of the tube portions before connection thereof. This enables a device that can be produced in the most compact and cost-effective manner possible. The possible compact design can in turn enable short paths of travel of the first tube portions, said paths having to be covered when producing the mechanical contact between the ends of said tube portions. This may reduce or eliminate positioning problems for example and in particular enables short "dock times", that is to say the tubes are separated and the first tube portions are connected within a relatively short period of time (for example in less than 10 s, for example in approximately 6 s). In addition, short tubes (which for example are at most 3 cm in length) can also be interconnected.

Since only one heating source has to be provided, it is also possible for example to provide a cover that can be assembled in a particularly simple manner, is as effective as possible and protects the device according to the invention against the infiltration of moisture. In addition, the first tube portions are moved so as to bring the ends thereof into contact substantially via a rotational movement of the receiving devices. Such a rotational movement can be generated by a relatively simple and robust mechanism, such that a device that is as reliable as possible and is stable in the long-term can be formed. An electric motor in particular is used to drive the receiving devices. For example, a DC motor is used in each case, which in particular has an encoder so as to be able to establish the position of the motor and therefore of the respective receiving device.

The first tube is connected for example to a first container (for example a blood bag) and the second tube is connected to a second container, which for example contains a blood additive. The method according to the invention can be used in this instance so as to interconnect the two containers by separating a "free" tube end (the "second tube portions") from both tubes and interconnecting ("docking") the remaining main tube portions (the "first tube portions"). Another application lies for example in the connection of a blood-conveying tube to a leukocyte filter.

It is noted that the elements already described further above in reference to the method according to the invention may of course also be implemented in this device. For example, the period of time that elapses from separation to contacting of the ends of the first tube portions is less than 0.1 s.

Furthermore, as already mentioned above, it is noted that the wording in accordance with which the first tube portions run "along a plane" of course also includes the case in which the first tube portions are held on the receiving devices such that they extend (at least in part) substantially in a straight line (that is to say along a longitudinal axis).

For example, at least one clamping device for clamping the tube arranged on the receiving device is assigned to each of the receiving devices, in particular so as to press the tube together and/or to hold it (for example on a support on which the clamping device is fixed) in preparation of the separation process. This clamping device is arranged in particular such that it is not entrained upon rotation of the receiving device. It is conceivable for the receiving devices and the respective clamping device to be arranged on a common support, wherein only the receiving devices (or at least one of the receiving devices) are rotatable relative to the support however, but not the clamping devices.

The clamping devices may each comprise two clamping jaws, between which the first or second tube is passed through and which can each be moved toward one another so as to clamp the tube between the clamping jaws. For example, the two clamping jaws (or just one of the clamping jaws) are rotated by means of an electric motor, which for example may also comprise an encoder, so as to be able to ascertain the position of the clamping jaws.

In accordance with an embodiment of the device according to the invention, the heating means comprise high-frequency voltage generation means, which are each electrically connected to at least one of the two clamping devices and are designed to introduce a high-frequency voltage into the respective clamping device so as to generate in the region of the clamping device an electrical high-frequency field. This high-frequency field heats (in particular via attachment to dipoles of the tube material) a region (the separating region) of the tube clamped by means of the clamping device.

For example, the clamping device also has two clamping jaws in this instance, between which the tube can be clamped, wherein the high-frequency voltage is fed at least into one of the two clamping jaws. In particular, the clamping jaw into which the high-frequency voltage is fed is formed from metal (for example from brass). In other words, at least one of the clamping jaws forms an HF electrode, which, in contrast to conventional HF electrodes, has a flat side for example, via which it bears against the tube in the clamped position.

The temperature of the tubes in the separating region and the size of the heated tube region can be controlled (for example regulated) for example via the duration and/or the intensity of the generated high-frequency field. For example, the plasticity (the hardness) of the heated tubes can be considered a measure for the temperature present in the tube material, wherein the plasticity of the tubes is ascertained for example on the basis of a measure of the force necessary to clamp the tubes by means of the clamping devices (for example, if the clamping devices are actuated by electric motor, on the basis of the current received by the electric motor, necessary to bring the clamping device, in particular the clamping jaws thereof, into a clamped position).

It is possible in particular for the motor current (or the motor voltage) to be predefined and for the position of the driven clamping jaw to be monitored with the aid of an encoder of the motor, wherein it is possible to determine when the clamping jaw bears against the tube on the basis of the received motor current. Once the clamping jaw bears against the tube, the high-frequency voltage is switched on. Depending on the temperature (that is to say the softness) of the tube, the clamping jaw will continue to move, wherein the tube starts to be torn apart (that is to say the movement generation means described further below are activated for example) in accordance with a predefineable value for example for the path covered by the clamping jaw once the high-frequency voltage has been switched on, that is to say at a specific softness of the tube.

The temperature of the tube also influences the adjustment, necessary to feed the high frequency, of a high-frequency circuit of the high-frequency voltage generation means, which can also be used for temperature control.

It is noted that the invention is not limited to heating by high-frequency field. Rather, other heating means may also be used, in particular those that enable contactless heating of the tube (for example an air heater or a laser).

In accordance with another development of the invention, at least one further clamping device for clamping a tube arranged on the receiving device is assigned to each of the receiving devices and is arranged on the respective receiving device such that it co-rotates upon rotation of the receiving device. The second clamping device is used in particular to hold the tube on the respective receiving device and/or to press together the tube before and after the separation. For example, this further clamping device likewise comprises two clamping jaws, which are connected to the receiving device. At least one of the two clamping jaws of the further clamping device may be formed from a plastic so as to prevent where possible an influence of a high-frequency field, should the heating means be based on heating by high-frequency field.

For example, one of the two clamping jaws of the further clamping device is fixedly connected to the receiving device, whereas the other clamping jaw is connected to said receiving device so as to be movable relative to the receiving device (for example by electric motor), such that the tube can be clamped between the two clamping jaws by moving (for example rotating) the movable clamping jaw toward the fixed clamping jaw.

The device according to the invention in particular comprises both a (first) clamping device not rotating with the assigned receiving device and a co-rotating (second) clamping device (per receiving device). For example, the first and second clamping devices are arranged such that the tube is exposed to a tensile and/or shear force exerted onto the respective tube as a result of a movement of the clamping devices relative to one another, said force leading to the separation of the tube in the heated separating region. It is possible for example for the heating means to heat the tube in the region of the two clamping devices and/or in the region between the two clamping devices such that the tube between the first and second clamping devices is separated as a result of the movement of said clamping devices relative to one another.

For example, inner sides of the ends of the first tube portion are pressed against one another by the second clamping device, whereby, as a result of the high temperature of the tube end, an integral bond between the inner sides is produced in particular, such that the end of each of the first tube portions is closed and the interior of the first tube portion thus remains sterile during the production of the mechanical contact between the first tube portions. The first clamping device closes the second tube portion analogously.

The first and second tubes are separated for example, as already indicated above, in that a tensile and/or shear force is exerted onto the tubes, that is to say the separating means comprise means for exerting a tensile and/or shear force that leads to the separation of the tubes in the heated separating region. The separating means for example comprise movement generation means for generating a movement of the first and/or second receiving device, a tensile and/or shear force being introduced into the first and/or second tube as a result of the movement of the first and/or second receiving device generated using the movement generation means and separates the first and/or second tube into the first and second tube portions.

The device according to the invention is not limited however to separating means that generate a tensile or shear force. Rather, the tubes may also be separated in another way, for example with use of a laser or a cutting edge. It also conceivable for different separating means to be used in combination with one another, for example one of the tubes can be separated by exerting a tensile force and the other tube can be separated by exerting a shear force.

Furthermore, a tensile and/or shear force on the tubes may also be generated by turning the first and/or second receiving device about its axis of rotation, which runs perpendicularly to the plane of the tube portion extending in the region of the receiving device. In other words, the separating means merely control the rotation of the receiving devices so as to generate a separating force (in particular a shear force) in the separating region of the tubes.

In accordance with one embodiment of the invention, the movement generation means comprise a first arm connected to the first receiving device and a second arm connected to the second receiving device, the two arms being interconnected such that they are rotatable relative to one another about a common axis of rotation in a scissor-like manner. For example, an end region of the first arm is coupled to the first receiving device and an end region of the second arm is coupled to the second receiving device. A region of the first arm spaced from the end region overlaps with a region of the second arm spaced from the end of the second arm, wherein coupling means (for example in the form of a pin) for example are provided in this overlapping region and couple the two arms so as to be rotatable relative to one another. By spreading apart the two arms, the receiving devices can be moved, more specifically in accordance with the movement of the arms about the axis of rotation about which the arms are rotated, that is to say in particular about an axis of rotation arranged outside the receiving devices. The movement generation means thus enable an additional movement of the receiving devices (in addition to a possible rotation about the axis of rotation of the receiving devices oriented perpendicularly to the plane along which the first tube portions extend).

With corresponding length of the arms (that is to say of the radius of the circular path over which the receiving devices are moved), a practically linear movement of the receiving devices can be generated.

It is also conceivable for the separating means to comprise translation generation means for generating a translation (that is to say a movement purely in a straight line or a movement at least substantially in a straight line) of the first and/or second receiving device, wherein a tensile and/or shear force on the first and/or second tube is likewise generated as a result of a translation produced by the translation generation means and thus causes the separation of the tubes. It is of course also possible for the separating means to have both rotation generation means and translation generation means, that is to say at least one of the two receiving devices may carry out both rotation and a translation movement (in particular simultaneously).

Furthermore, the device may comprise a first clamping device (as already described above), which is assigned to one of the receiving devices and in which the tube can be clamped and which is not entrained with a rotational and/or translation movement of the receiving device. The device (likewise as described above) further comprises for example a second clamping device, which is entrained with rotation and/or translation of the receiving device, such that a tensile and/or shear force can be generated by translatory and/or rotary movement of the receiving device relative to the (fixed) first clamping device. Once the tube has been separated, the first clamping device then clamps the produced free end of the second tube portion and the second clamping device clamps the free end of the first tube portion.

In accordance with a further embodiment of the invention, the first and/or the second receiving device are each designed in a plate-like manner, in particular in the form of a disk (that is to say in the form of a plate that is at least approximately circular in plan view). For example, the disk is rotatable about an axis of rotation that extends through its midpoint.

In accordance with another embodiment of the invention, the first and/or the second receiving device each comprise a receiving body that has a recess (for example in the form of a groove) in a side oriented parallel to the axis of rotation (which is assigned to the respective receiving device) for insertion of the first or second tube. The receiving device is for example embodied in the form of a plate, wherein the receiving body is arranged as a prism-like body on one of the main faces of the plate. The aforementioned recess is then located for example in a side of the prism-like body extending perpendicularly to the main face of the plate.

The above-described device is used in particular to carry out a method for the sterile connection of tubes, said method comprising the following steps:
  providing a first and a second tube;
  heating the first and second tube in a separating region;
  separating the first and second tube in the heated separating region into a first and a second tube portion; and
  producing mechanical contact between an end of the first tube portion of the first tube and an end of the first tube portion of the second tube;
  wherein the mechanical contact is produced with rotation of the first and/or second tube portion about an axis of rotation that runs at least approximately perpendicularly to a plane along which the first tube portion extends at least in part.

The invention will be explained in greater detail hereinafter on the basis of exemplary embodiments with reference to the figures, in which:

FIGS. 3A-3F show the operating principle of movement generation means;

FIGS. 9A-9F show a third embodiment of clamping devices of the device according to the invention with an inserted tube of a first diameter; and FIGS. 10A-10F show the third embodiment of clamping devices of the device according to the invention with an inserted tube of a second diameter.

Figure 1A:
FIGS. 1A-1D show schematic method steps of a method according to an exemplary embodiment of the invention.
Figure 1B:
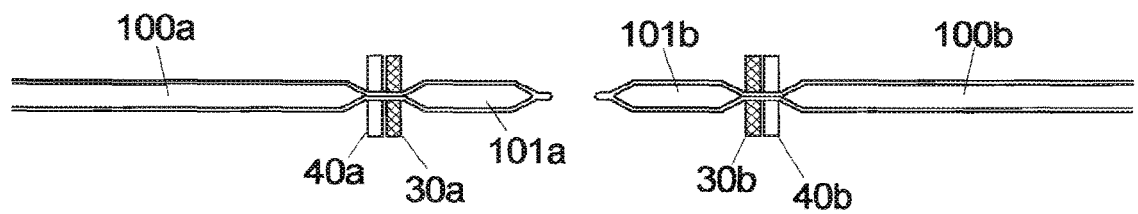

FIGS. 1A-1D illustrate a method for the sterile connection of tubes according to an exemplary embodiment of the invention. In accordance with this exemplary embodiment, a first and a second tube 1a, 1b, which are each formed from a thermoplastic material, are provided and are to be interconnected. The tubes 1a, 1b each have a closed end and are connected for example to a liquid reservoir via their respective other end (not illustrated) (FIG. 1A).

Before the tubes 1a, 1b are connected, the tubes are each separated into a first tube portion 100a, 100b and a second tube portion 101a, 101b (which comprises the free end of the respective tube). In order to prepare for the separation of the tubes, said tubes are each clamped by means of a first clamping device 30a, 30b and a second clamping device 40a, 40b. A high-frequency electrical voltage is conveyed to the first clamping devices 30a, 30b with use of heating means in the form of high-frequency voltage generation means (not illustrated), such that a high-frequency electrical field is produced in the region of the first clamping devices 30a, 30b and heats each of the tubes 1a, 1b (for example to at least 200° C.) in an intended separating region, that is to say in particular in the region of the first clamping devices 30a, 30b and in a region between the first and the second clamping devices 30a, 30b and 40a, 40b. In particular, the tubes are torn apart from one another in the region between the first and second clamping devices 30a, 30b and 40a, 40b, which will be explained in greater detail further below in reference to FIGS. 2A-2H. The method according to the invention and accordingly the device according to the invention thus enable contactless separation of the tubes.

Figure 1C:
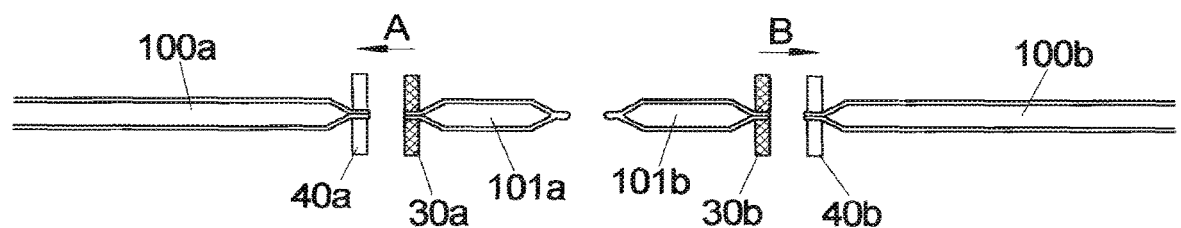

Once the separating region of each of the tubes 1a, 1b has been heated to a temperature above the melting point of the tube material, that is to say once the tube material in the separating region is in the thermoplastic state, a tensile force is exerted onto each of the tubes 1a, 1b along the longitudinal axis thereof, such that said tubes are torn apart from one another in the softened separating region (FIG. 1C). In the example of FIGS. 1A-1D the tensile force is generated by mounting each of the clamping devices 30a, 30b fixedly and by exerting onto the clamping devices 40a, 40b a force away from the clamping device 30a, 30b (indicated in FIG. 1C by the arrows A, B).

Figure 1D:
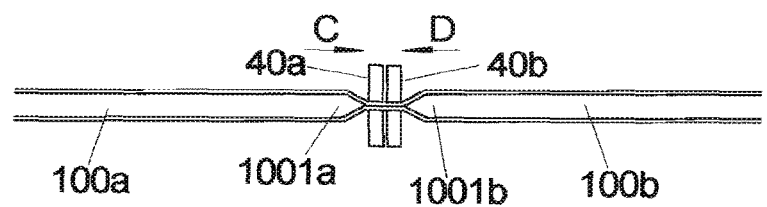

For example, the heating means are switched off after separation of the tubes 1a, 1b (or shortly before), that is to say the introduction of the high-frequency voltage into the clamping devices 30a, 30b is terminated. It is also conceivable however for the heating means to remain switched on after the separation of the tubes, for example so as to reliably close the remaining tube portions 101a, 101b, in which liquid may be located. Once the tubes 1a, 1b have been separated, mechanical contact is produced between the end 1001a of the first tube portion 100a, formed by the separation of the first tube 1a, and the end 1001b of the first tube portion 100b of the second tube 1b, formed by the separation of the second tube 1b. To this end, the now separate first tube portions 100a, 100b are in particular initially moved away from the second tube portions 101a, 101b and are aligned along a common axis. The first tube portions 100a, 100b are then moved toward one another (arrows C, D), until their two ends 1001a, 1001b come into mechanical contact with one another (FIG. 1D).

It is noted that the heating means may also remain switched on until the tube ends 1001a, 1001b are interconnected. However, the ends 1001a, 1001b of the first tube portions 100a, 100b are positioned at a distance from the heating means (in particular from the HF clamping devices 30a, 30b) after the separation of the tubes, such that there is no heating of the ends 1001a, 1001b by the heating means.

The mechanical contact between the ends 1001a, 1001b is produced after the separation of the tubes 1a, 1b so quickly that the two ends 1001a, 1001b each still have a temperature above the melting point of the tube material when they come into contact with one another, such that they form an integral bond with one another (that is to say are welded to one another) without the need for renewed heating of the ends 1001a, 1001b.

FIGS. 2A to 2H each show different steps during the production of a sterile connection between two tubes with use of a device according to a first exemplary embodiment of the invention. According to FIG. 2A, the device 10 comprises a first receiving device in the form of a first disk 20a and a second receiving device in the form of a second disk 20b. The disks 20a, 20b are each mounted rotatably about an axis of rotation that extends perpendicularly to the respective main faces of said disks and through the midpoint thereof.

A first tube 1a is received on the first disk 20a and a second tube 1b is received on the second disk 20b. The tubes 1a, 1b are each guided along a receiving body 21a, 21b arranged on the respective disk 20a, 20b, wherein the receiving bodies 21a, 21b each have a groove 211a, 211b for guiding the tube (see the detail of the device 10 illustrated in cross section in the bottom left-hand corner next to the primary illustration in FIG. 2A), which extends at least over part of a side of the prism-like receiving body 21a, 21b facing the tube 1a or 1b respectively.

The device 10 further comprises a guide body 22, which is assigned jointly to both disks 20a, 20b, (but is arranged separately relative thereto) and comprises a first groove 221a facing the first tube 1a and a second groove 221b facing the second tube 1b, which are used to guide the respective tube; see the cross-sectional illustration already mentioned above of a detail of the device 10 in FIG. 2A.

In addition, the device 10 comprises two first clamping devices 30a, 30b, which are assigned to the first disk 20a and to the second disk 20b respectively. The first clamping devices 30a, 30b have a first clamping jaw 301a, 301b respectively, which are mounted rotatably about an axis of rotation extending perpendicularly to the main face of the disks 20a, 20b (that is to say also perpendicularly to a plane or longitudinal axis along which the tube 1a, 1b extends at least in the region of the receiving body 21a, 21b). The tubes 1a, 1b are clamped respectively between the clamping jaws 301a, 302a and 301b, 302b by rotation of the first clamping jaws 301a, 301b (see FIG. 2C explained in greater detail further below).

The device 10 also comprises two second clamping devices 40a, 40b, which are likewise assigned to one of the disks 20a, 20b respectively. The second clamping devices 40a, 40b have a respective first clamping jaw 401a, 401b arranged on the disk 20a, 20b, but rotatable relative to the respective disks 20a, 20b, and a second clamping jaw 402a, 402b arranged fixedly (non-rotatably) on the disks 20a, 20b. By rotating the first clamping jaws 401a, 401b in the direction of the second clamping jaws 402a, 402b respectively, the tube can be clamped above the first clamping device (that is to say on a side of the first clamping device 30a, 30b facing away from the free end of the tubes 1a, 1b). For example, the clamping jaws 401a, 401b are guided within a correspondingly embodied recess in the respective receiving body 21a, 21b.

Once the tubes 1a, 1b have been inserted into the respective groove 211a, 221a or 211b, 221b in the receiving bodies 21a, 21b and the guide body 22, the disks 20a, 20b are rotated slightly toward the guide body 22, that is to say the first disk 20a rotates in an anti-clockwise direction and the second disk 20b rotates in a clockwise direction, such that the receiving bodies 40a, 40b are moved toward the guide body 22, whereby the tube 1a, 1b is clamped slightly between the receiving bodies 40a, 40b and the groove 221a, 221b, assigned to the respective tube 1a, 1b, in the guide body 22.

Due to the at least approximately V-shaped or U-shaped embodiment of at least one of the grooves 211a, 211b or 221a, 221b, the tube is centered, that is to say is moved away (vertically) slightly from the disks 20a, 20b from its position after insertion, such that the midpoint of the portion of the tubes 1a, 1b clamped between the receiving bodies 40a, 40b and the guide body 22 is arranged at a defined distance from the upper face of the disks 1a, 1b, irrespectively of the diameter of the tube, that is to say is centered relative to the grooves 211a, 211b and 221a, 221b. This centering of the tubes in particular enables a connection of tube portions of different diameter, which will be discussed in greater detail further below. The centering process is illustrated in particular in the cross-sectional illustrations to the left beside the primary illustration in FIG. 2B, wherein it should be noted that the receiving body 211a and the guide body 22 are arranged in succession along the tube 1a.

Figure 2A:
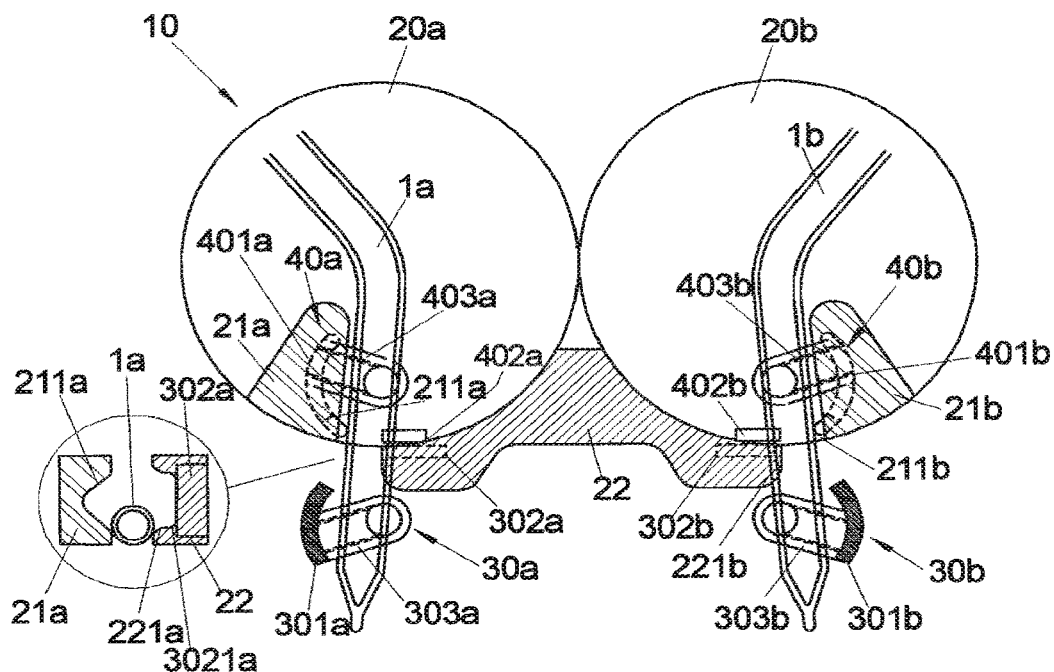
FIGS. 2A-2H show the operating principle of a device according to a first exemplary embodiment of the invention.
Figure 2B:
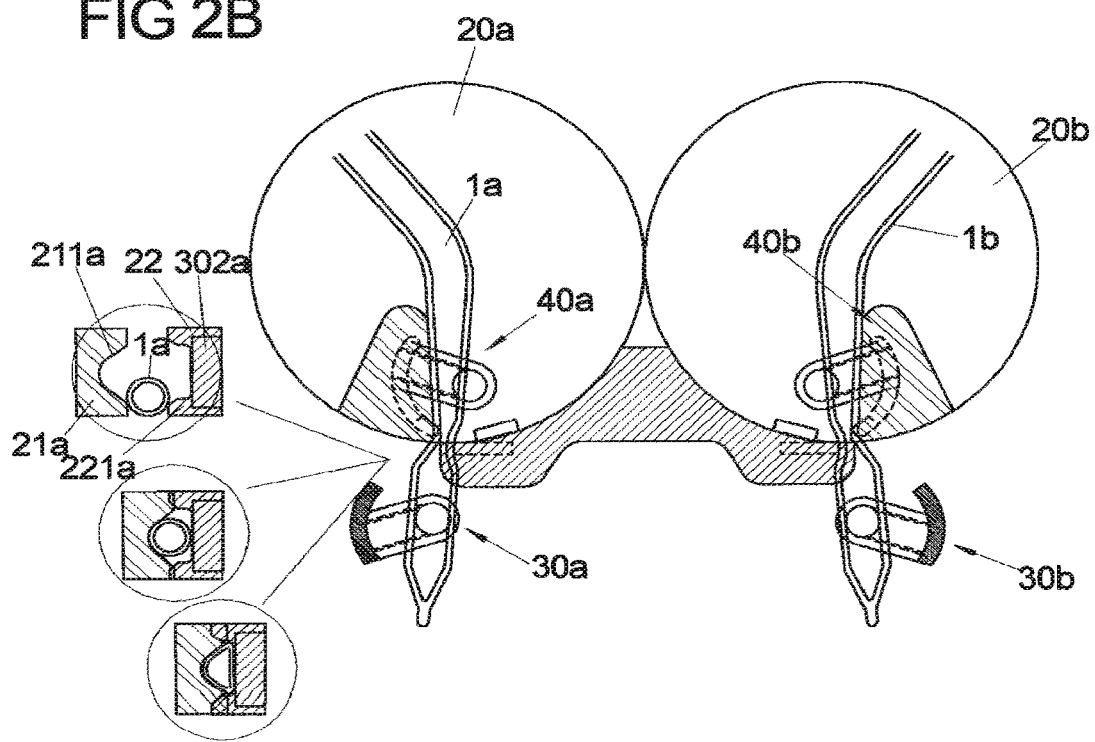
Figure 2C:
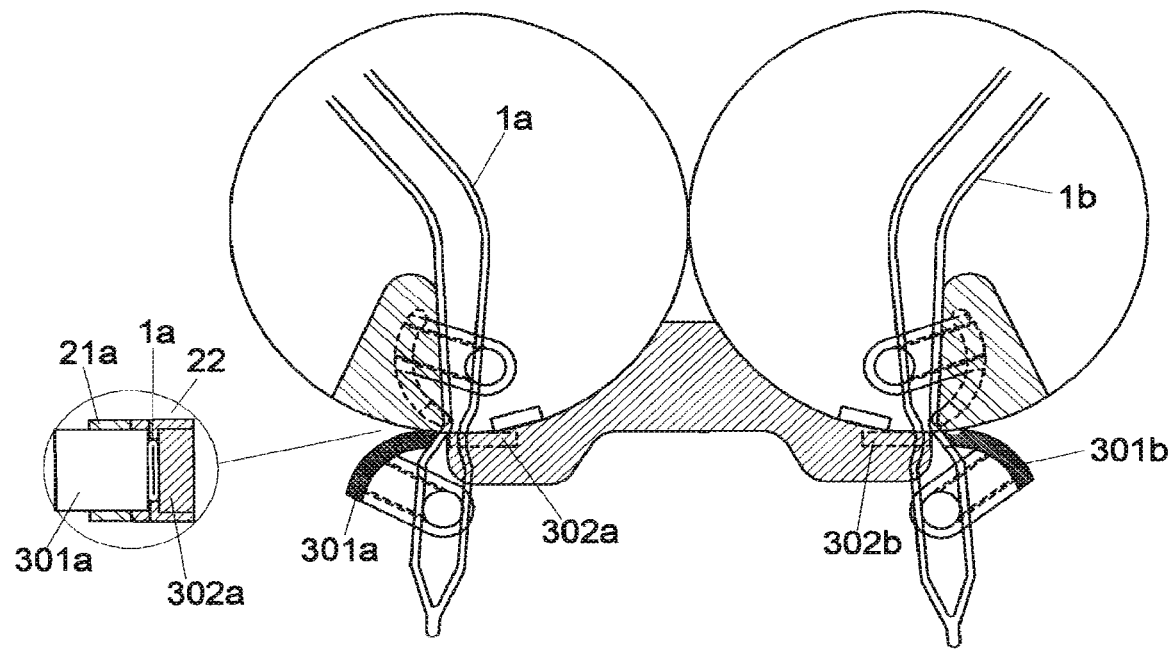

After the initial rotation of the disks 20a, 20b according to FIG. 2B, the first clamping jaw 301a, 301b of the first clamping devices 30a, 30b are rotated toward the respective tube 1a, 1b until the tube 1a, 1b is clamped between the two clamping jaws 301a, 302a and 301b, 302b; see FIG. 2C. The first clamping jaws 401a, 401b of the second clamping device 40a, 40b are then also activated such that they likewise pivot in the direction of the tube and press and therefore clamp the tube 1a, 1b against the respective second clamping jaws 402a, 402b; see FIG. 2D. The pivoting movement of the first clamping jaws 301a, 301b and 401a, 401b is generated in particular via electric motors, wherein an electric motor is in particular assigned to each clamping jaw. The electric motors are arranged for example on a rear face (that is to say a side facing away from the tubes 1a, 1b) of the clamping jaws. The clamping jaws are pivotably connected in particular via arms 303a, 303b, 403a, 403b to a shaft of the respective motor.

The disks 20a, 20b are at least approximately rotated back into their starting position shown in FIG. 2A, either at the same time as, or before, the pivoting motion of the first clamping jaws 401a, 401b. The first clamping devices 30a, 30b are activated before the second clamping devices 40a, 40b, in particular so as to counteract a build-up of pressure in the remaining tube portions 101a, 101b, which could lead to a ripping or bursting of the remaining tube portions. It is therefore of course also conceivable for the second clamping devices 40a, 40b to be activated before the first clamping devices 30a, 30b.

The device 10 further comprises heating means for heating a separating region of the tubes 1a, 1b, in which a first tube portion in the form of the main tube portion 100a, 100b and a second tube portion in the form of an end tube portion 101a, 101b adjoin one another respectively. The heating means are designed in the form of high-frequency voltage generation means (in particular comprising a high-frequency voltage source, which is not illustrated in FIGS. 2A-2H), which are electrically connected to the second, metal clamping jaws 302a, 302b ("hot electrodes") of the first clamping devices 30a, 30b and which introduce a high-frequency voltage into the clamping jaws 302a, 302b after activation (indicated in FIG. 2E by jagged arrows).

The first, movable clamping jaws 301a, 301b are at earth potential in particular. The HF clamping jaws 302a, 302b are arranged in a recess in the guide body 22 adjoining the grooves 221a, 221b, said guide body possibly being formed from an electrically insulating material, for example at least in part. The HF clamping jaws 302a, 302b are additionally positioned such that they each adjoin the groove 221a, 221b via a substantially flat clamping side 3021a, 3021b, with which they bear against the tube in the clamped position of the clamping devices 30a, 30b and introduce the high-frequency voltage into the tube, that is to say the clamping sides 3021a, 3021b form a base of the respective groove.

The high-frequency voltage generation means generate via the clamping jaws 301a, 302a, 301b, 302b an electrical high-frequency field in the separating region of the tubes 1a, 1b (that is to say in a region in the vicinity of the clamping jaws 301a, 301), which heats each of the tubes in this separating region. Once the separating region has been heated or during the heating process, a movement of the disks 20a, 20b away from the first clamping devices 30a, 30b is initiated (see FIG. 2F). The device 10 has movement generation means, which will be explained by way of example with reference to FIGS. 3A-3F, in order to generate this movement.

Figure 2D:
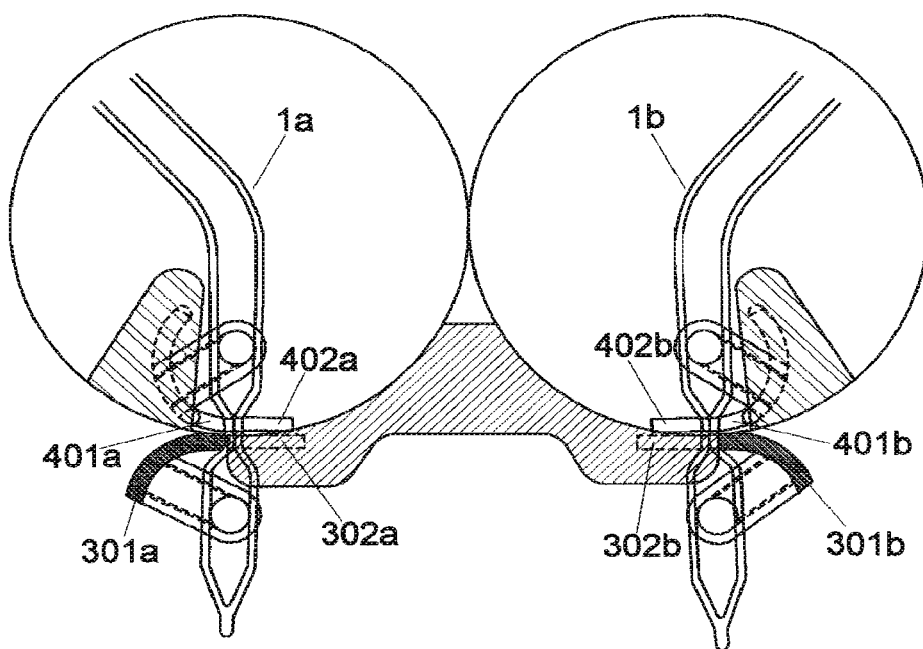
Figure 2E:
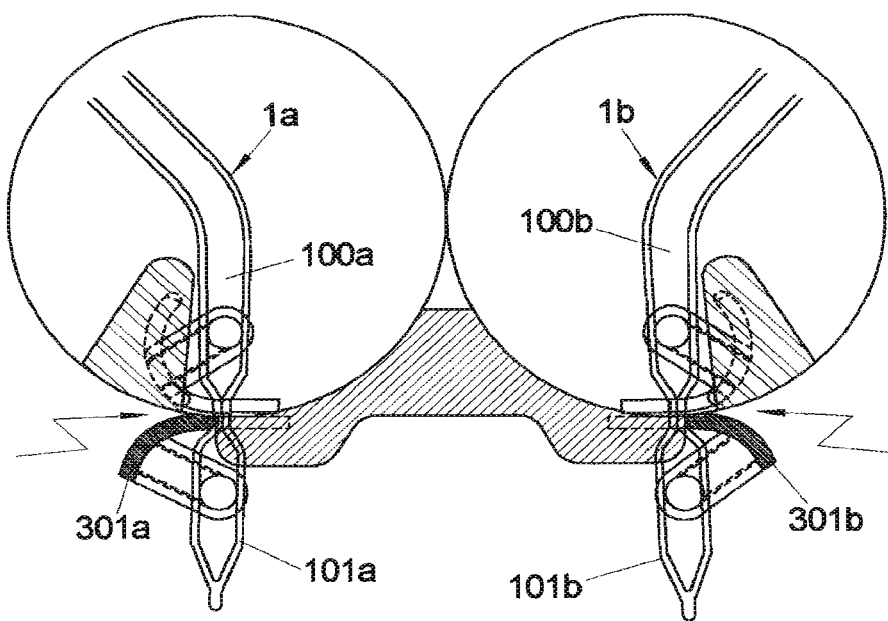
Figure 2F:
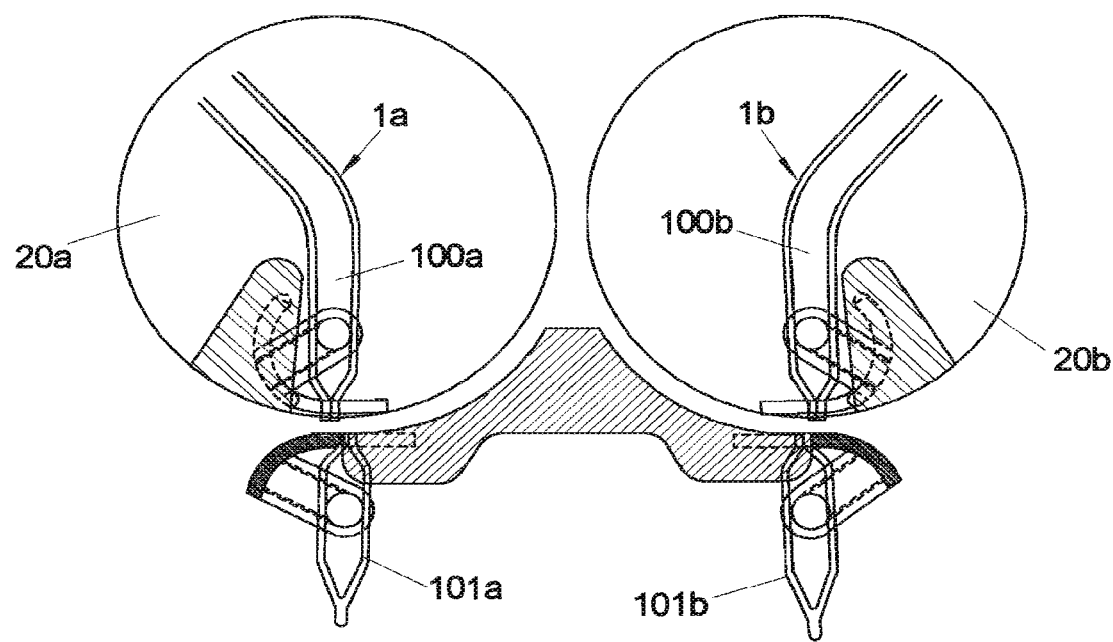

Due to the movement of the disks 20a, 20b away from the first clamping devices 30a, 30b, a tensile and shear force is exerted onto the tubes 1a, 1b, such that they are drawn away from one another in the separating region and are ultimately torn apart from one another, that is to say the main tube portions 100a, 100b are separated from the end tube portions 101a, 101b. It is noted that the movement of the disks 20a, 20b illustrated in FIG. 2F is not absolutely necessary to separate the tubes. Rather, it is also conceivable that a separating force is generated by displacing the disks 20a, 20b merely in rotation about their axis of rotation extending through their midpoint, without moving the disks 20a, 20b away from the guide body 22.

A smooth tear-off edge is produced in particular between the tube portions 100a, 101a and 100b, 101b above the first and second clamping jaws 301a, 302a, 301b, 302b (that is to say the "hot" HF electrodes), which is attributed in particular to the fact that an improved transport of heat from the tube 1a, 1b is produced via the first clamping jaws 301a, 301b formed from metal compared to the transport of heat in the region above the clamping jaws 301a, 301b (that is to say in the region between the clamping jaws 301a, 301b and the first clamping jaws 401a, 401b of the second clamping device 40a, 40b), whereby a temperature gradient occurs in the tube on the upper side (that is to say a side facing toward the second clamping device 40a, 40b) of the first clamping jaws 401a, 401b, wherein the tubes are preferably torn apart from one another in the region of this temperature gradient under the influence of the tensile or shear force. In particular, the temperature gradient exists at the surface of the tubes, wherein it is possible for the surface of the tubes to have a greater temperature between the clamping devices 30a, 30b and 40a, 40b than the surface of the tubes in the region of the first clamping devices 30a, 30b (that is to say between the clamping jaws 301a, 302a and 301b, 302b).

In particular, the clamping jaws used as high-frequency electrodes have a flat side, via which they bear against the tube in the clamped position so as to generate a most uniform field possible in the tube and also to implement the best possible dissipation of heat away from the tube.

Figure 2G:
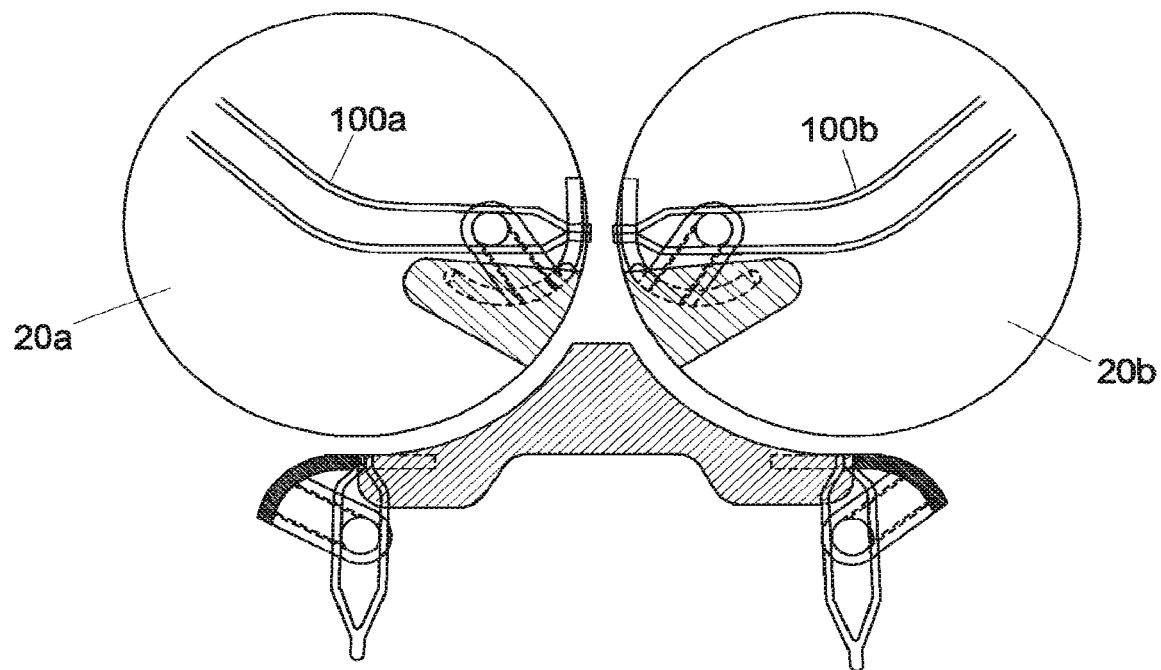

Once the tubes 1a, 1b have been separated into the main tube portions 100a, 100b and the end tube portions 101a, 101b, the disks 20a, 20b are rotated in such a way that the ends of the main tube portions 100a, 100b produced by the separation of the tubes 1a, 1b and held by the second clamping devices 40a, 40b are moved toward one another; see FIG. 2G. To this end, the first disk 20a is rotated in an anti-clockwise direction about the axis of rotation oriented perpendicularly to the main faces of the disk and therefore also perpendicularly to a plane along which a part (that runs in the region of the receiving body 40a) of the main tube portion 100a extends. An analogous rotational movement is performed by the second disk 20b, but in a clockwise direction.

Figure 2H:
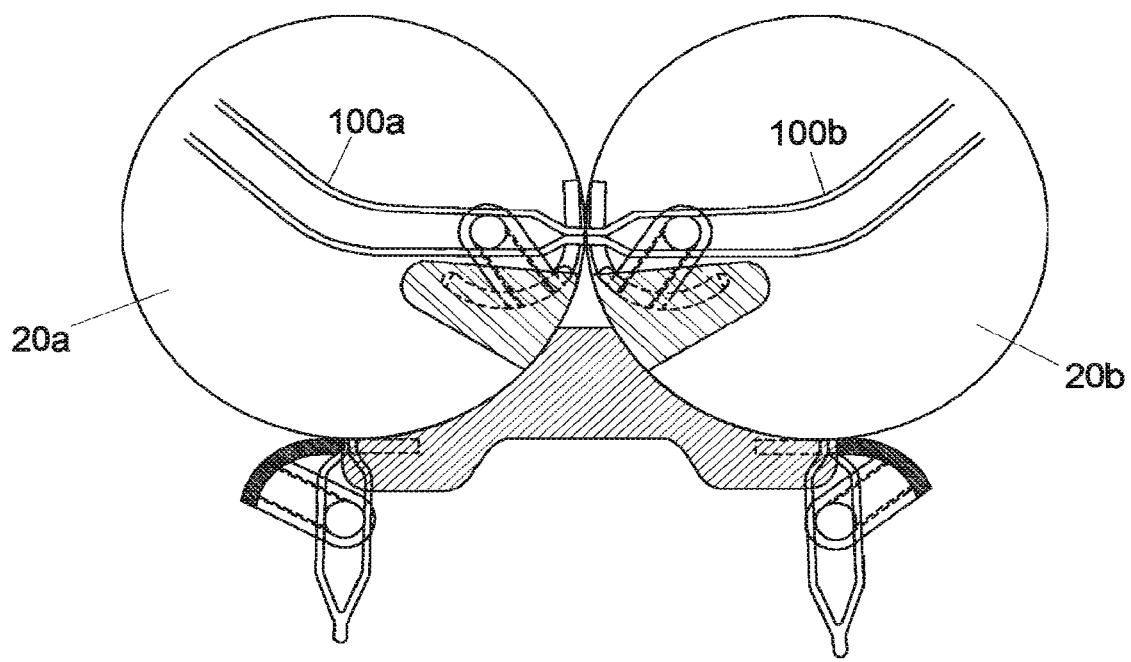

The disks 20a, 20b are each rotated about approximately 900, such that the two ends of the main tube portions 100a, 100b lie opposite one another along a common longitudinal axis after the rotation of the disks 20a, 20b. The two disks 20a, 20b are then moved toward one another such that the end faces of the ends of the main tube portions 100a, 100b lying opposite one another along the common longitudinal axis contact one another (FIG. 2H). In particular, the disks 20a, 20b are rotated about their respective axis of rotation and the disks are moved toward one another so quickly that the ends of the main tube portions 100a, 100b, as a result of the heating according to FIG. 2E, still have such a temperature even once the heating means have been switched off that they form an integral bond with one another, that is to say are welded to one another, when they come into mechanical contact with one another in accordance with FIG. 2H, without the need for renewed heating.

After a cooling phase (for example at least 4 s), the second clamping jaws 401a, 401b of the second clamping device 40a, 40b can also be released and the tube produced by connection of the main tube portions 100a, 100b can be removed from the device 10. The invention is of course not limited to a specific cooling time; shorter or longer cooling times may also be necessary, for example according to the nature of the tube. In particular, the tube must have sufficient strength after the cooling time so that it can be removed reliably from the device and used.

Due to the high temperature of the ends of the main tube portions 100a, 100b, a material skin is formed in particular, which closes the cross section of the main tube portions 100a, 100b (a closure of the end tube portions 101a, 101b is also produced analogously). This is assisted by the clamping of the tube by means of the first and second clamping devices, whereby a connection between inner sides of the clamped (and heated) tube portions is produced in particular. The main tube portions are thus closed in particular in a sterile manner during the production of the mechanical contact. Once the main tube portions 100a, 100b have been connected, this closure may continue to exist, but can be opened by light (in particular manual) external pressure onto the connection point. Due to the continued existence of the closure, even after the connection of the first tube portions, it is possible to first check whether the correct tubes (that is to say the correct containers connected to these tubes) have actually been connected. This can be checked for example by scanning in labels of the connected containers. Only if this check confirms that the correct containers have been connected is the closure between the tube portions opened by pressure on the connection point.

FIGS. 3A to 3F show an embodiment of a device 10, which has movement generation means for generating a movement of the disks 20a, 20b so as to distance them, as shown in FIG. 2F, from the first clamping devices 30a, 30b and to move them toward one another once the ends of the main tube portions have been aligned, as illustrated in FIG. 2H.

The device accordingly comprises movement generation means 50, which generate a rotation of the disks 20a, 20b about an axis of rotation running outside the disks. The movement generation means 50 comprise a first arm 51, which is connected via connection means 511 (for example in the form of a screw) at least approximately to a midpoint of the first disk 20a, and a second arm 52, which is connected via analogous connection means 521 to the midpoint of the second disk 20b.

The two arms 51, 52 are coupled to one another in a scissor-like manner such that they are rotatable relative to one another about a common axis of rotation 53. A pin extends through aligned openings in the arms 51, 52 for this purpose. By spreading apart from one another ends 512, 513 of the arms 51, 52 facing away from the disks 20a, 20b, a movement of the ends 514, 515 of the arms 51, 52 connected to the disks 20a, 20b and therefore a movement of the disks 20a, 20b can thus be generated.

Due to the rotatable mounting about the center of rotation 53, a rotational movement of the disks 20a, 20b (away from one another or toward one another) over a circular path about the axis of rotation 53 is generated. The ends 512, 513 of the arms 51, 52 facing away from the disks 20a, 20b are spread apart from one another via a rotatable annular disk 55, which is connected via connection elements (for example formed in an approximately rod-shaped manner) 56, 57 to the ends 512, 513 of the arms 51, 52. In this case, an end of the first connection element 57 is connected rotatably to the end 513 of an arm 52, whereas the other end of the connection element 57 is fastened rotatably and eccentrically to the annular disk 55. Analogously, the second connection element 56 is coupled to the arm 51 and the annular disk 55, wherein the connection points (which are formed for example by a pin-like connection between the annular disk 55 and the connection elements 56, 57) between the connection elements and the annular disk lie opposite one another along a radius of the annular disk 55.

The annular disk is driven by an electric motor for example, of which the shaft is connected to the annular disk, in particular in a central opening in the annular disk. The electric motor is located for example on a side of the annular disk that faces away from the disks 20a, 20b. All elements that are moved during production of the tube connection (the means 50, the disks 20a, 20b and the movable clamping jaws of the clamping devices 30a, 30b, 40a, 40b) are therefore in particular driven by electric motor. For example, all electric motors are equipped with an encoder such that the position of each of the moved elements can be determined. For example, the disks 20a, 20b and the clamping devices 30a, 30b, 40a, 40b are arranged (at least in part) on one side of a support (for example in the form of a metal or plastic plate), whereas the electric motors for example are arranged on an averted side of the support, wherein a shaft of the motors passes through the support in each case.

Figure 3C:
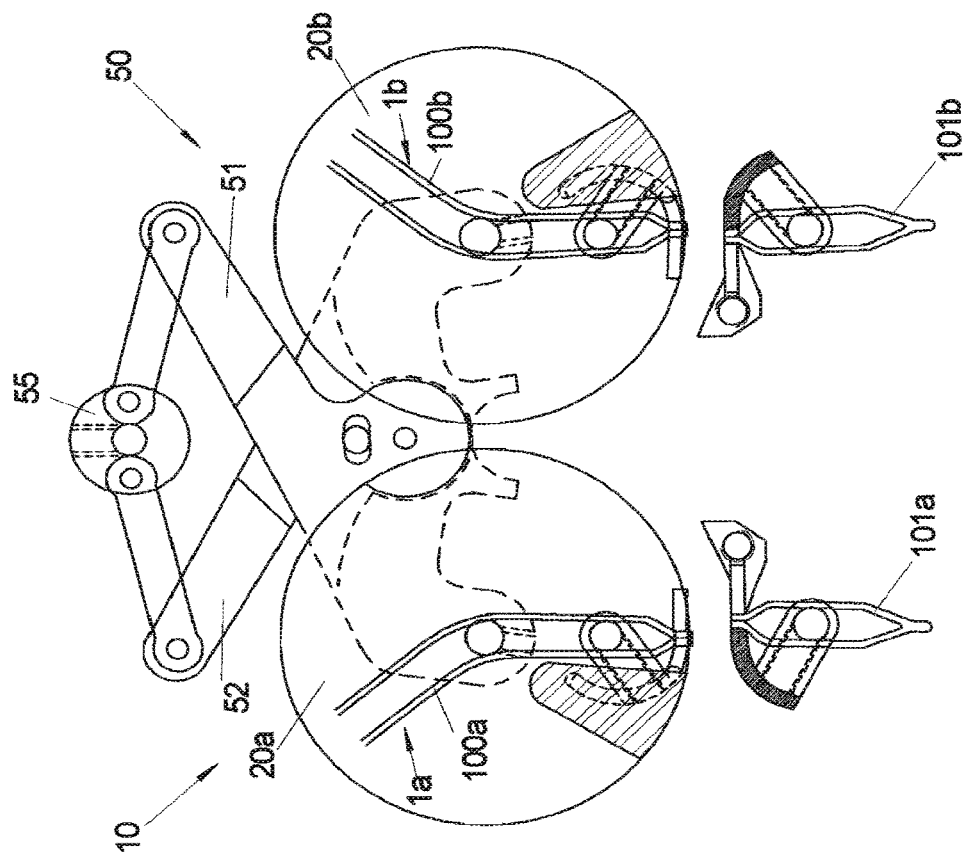
Figure 3D:
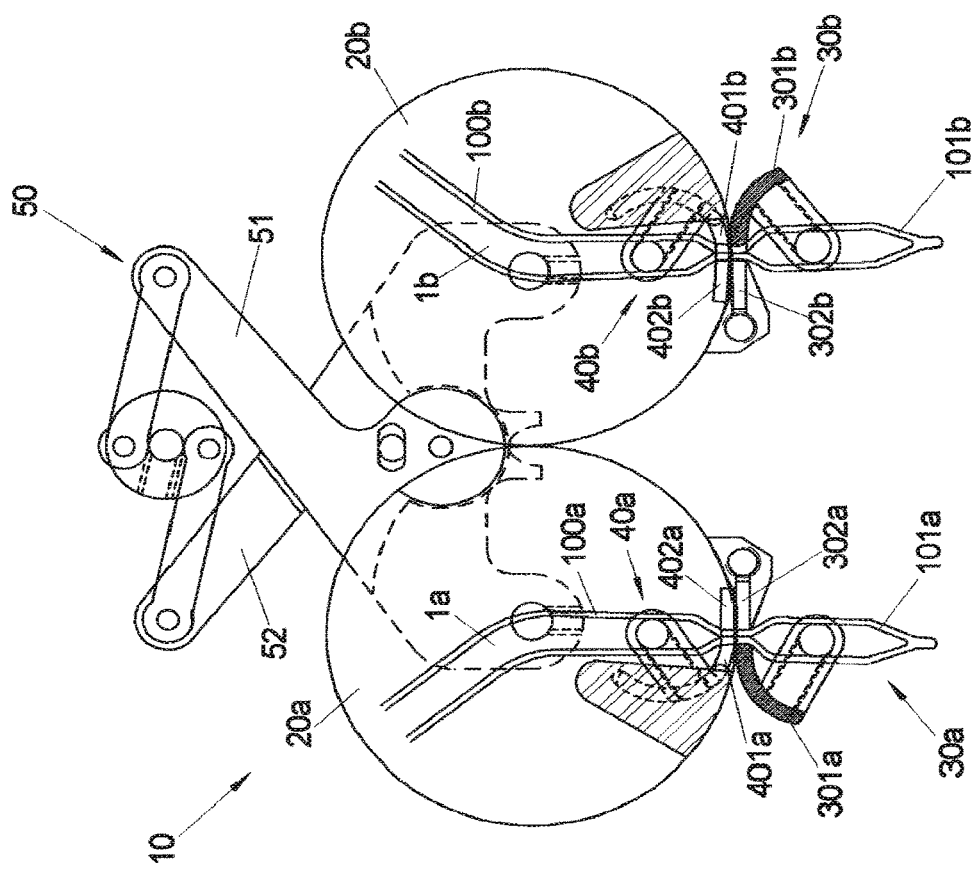
Figure 3F:
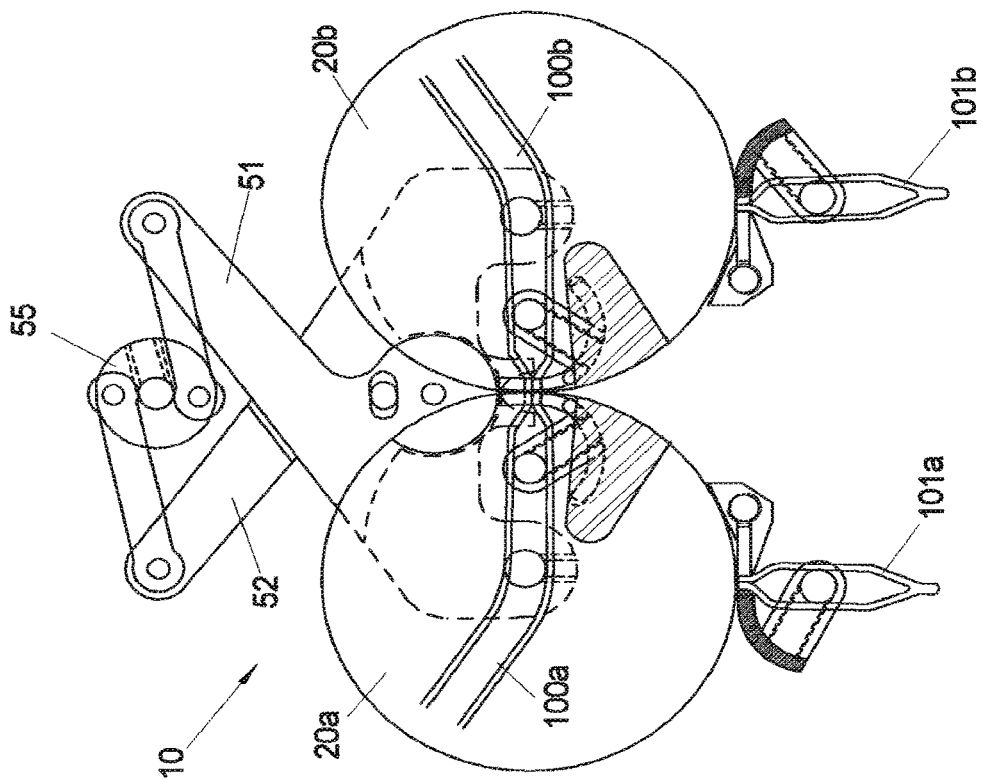
Figure 3E:
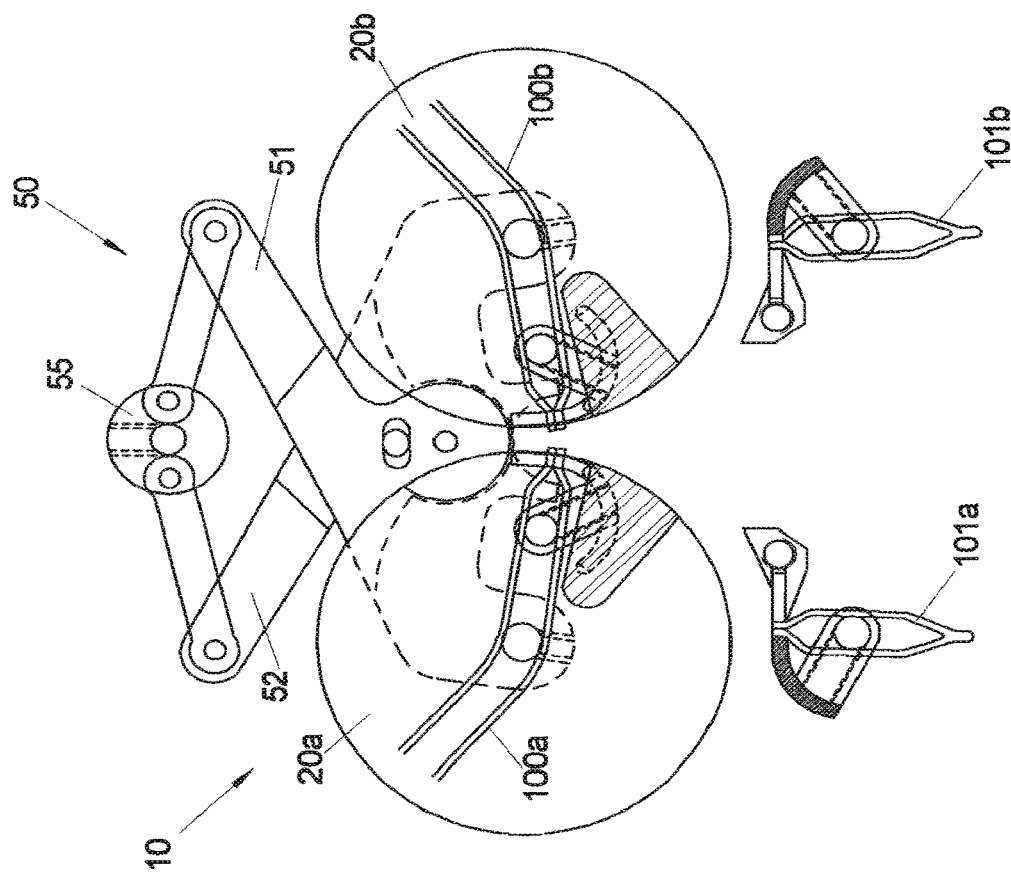

FIG. 3A corresponds to the starting position of the device 10 (in accordance with FIG. 2A). FIG. 3B shows the clamping of the tube by means of the first clamping devices 30a, 30b, analogously to FIG. 2C. The movement generation means 50 are again located in this instance in their starting position. Only after the activation of the second clamping devices 40a, 40b also (analogously to FIG. 2E) and heating of the tubes 1a, 1b is the annular disk 55 rotated so as to cause the upper ends 512, 513 of the arms 51, 52 to spread apart from one another and to therefore cause the ends 514, 515 of the arms 51, 52 connected to the disks 20a, 20b to spread apart from one another (FIG. 3D).

As a result of the fact that the lower ends 514, 515 are spread apart from one another, the disks move away from one another over a circular path about the center of rotation 53, whereby the tubes are torn apart from one another in the heated separating region (see FIG. 2F). The disks 20a, 20b are rotated about their axes of rotation running through their respective midpoints, either at the same time as, or after, the movement of the disks 20a, 20b about the center of rotation 53, such that the ends of the main tube portions 100a, 100b produced as a result of the fact that the tubes 1a, 1b are torn apart from one another are brought toward one another; see FIG. 3E.

After rotation of the disks 20a, 20b about their respective midpoint (by approximately 900), the disks 20a, 20b and therefore also the ends to be connected of the main tube portions 100a, 100b are still distanced from one another due to the rotation, generated by the means 50, about the center of rotation 53. Only as a result of further rotation of the annular disk 55 are the lower ends 514, 515 of the arms 51, 52 again brought toward one another, such that the circular disks 20a, 20b move toward one another and the ends of the main tube portions 100a, 100b come into contact with one another; see FIG. 3F.

FIGS. 4A to 4G concern a device according to a further exemplary embodiment of the invention. The device 10 in this exemplary embodiment corresponds in principle to the design of the device in FIGS. 2A to 2D. However, the receiving bodies 40a, 40b are formed slightly differently and in particular are arranged such that they are oriented in the starting position (FIG. 4A) of the disks 20a, 20b such that their sides, in each of which the groove for receiving the tube 1a, 1b is provided, extend away from one another.

In particular, the receiving sides of the receiving bodies 40a, 40b are aligned obliquely relative to a vertical (for example a plane of symmetry of the device), such that the tubes 1a, 1b inserted into their grooves run toward one another, that is to say tube portions in the vicinity of the first clamping device 30a, 30b are arranged closer to one another in the starting position of the device 10 compared to tube portions located at a greater distance from the first clamping device. This orientation of the receiving bodies 21a, 21b in particular enables facilitated insertion of the tubes into the device 10.

Furthermore, the clamping jaws 301a, 302a and 301b, 302b of the first clamping devices 30a, 30b are arranged in a mirrored manner compared to the exemplary embodiment in FIGS. 2A to 2H, that is to say the first clamping jaw 301a of the clamping device 30a is rotated in an anti-clockwise direction so as to bring them into the clamped position, and the first clamping jaw 301b of the clamping device 30b is rotated in a clockwise direction. The receiving bodies 21a, 21b and the first clamping devices 30a, 30b are not illustrated in FIGS. 4E to 4G for reasons of clarity.

Figure 4A:
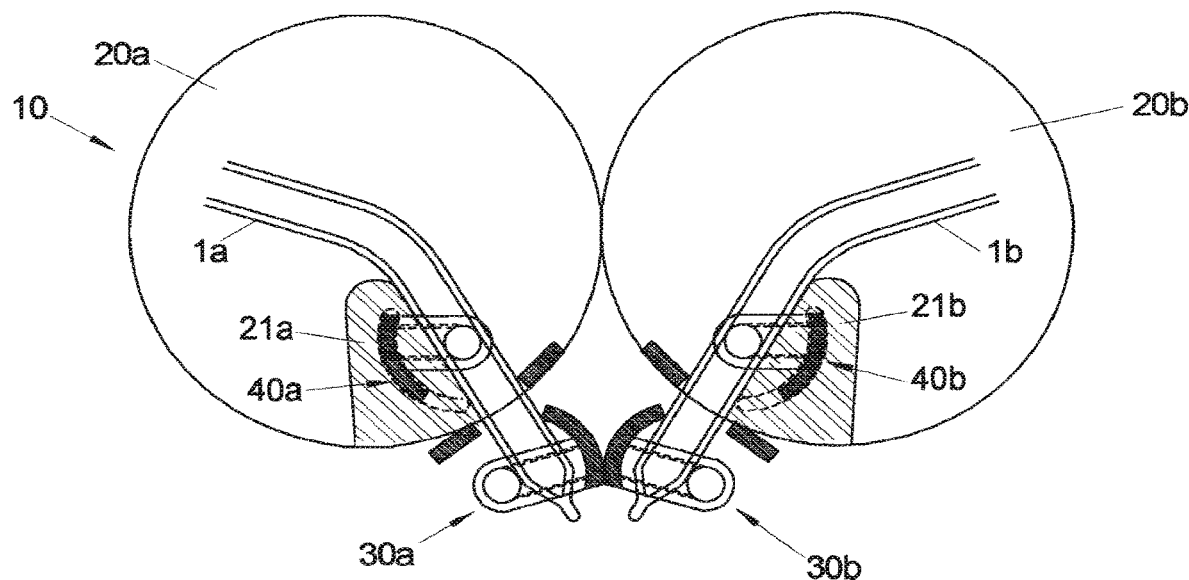
FIGS. 4A-4G show the operating principle of a modification of the device from FIGS. 2A-2H.
Figure 4B:
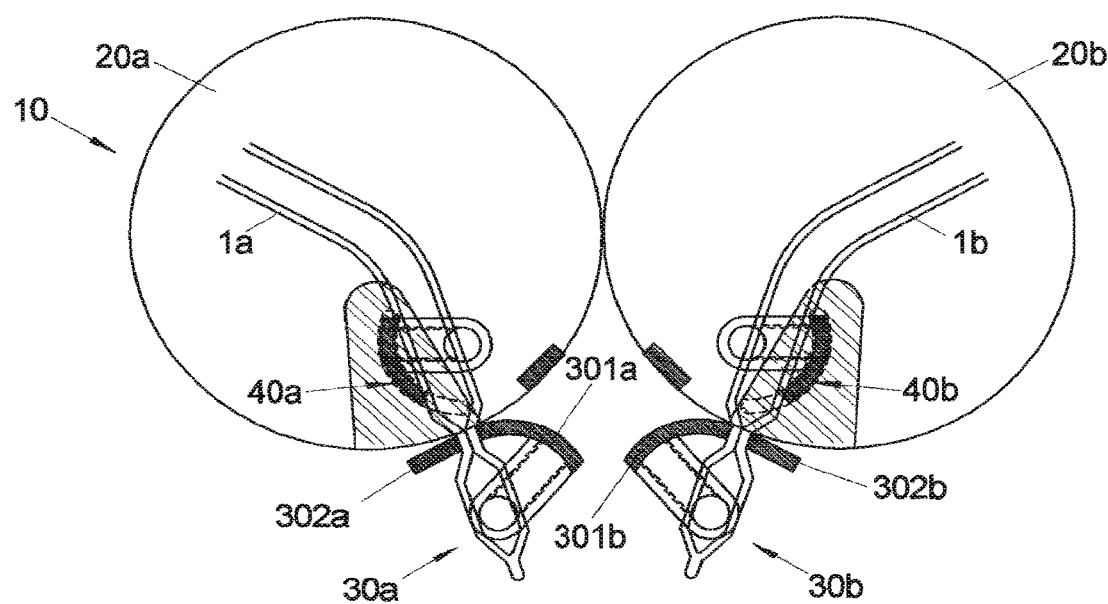
Figure 4C:
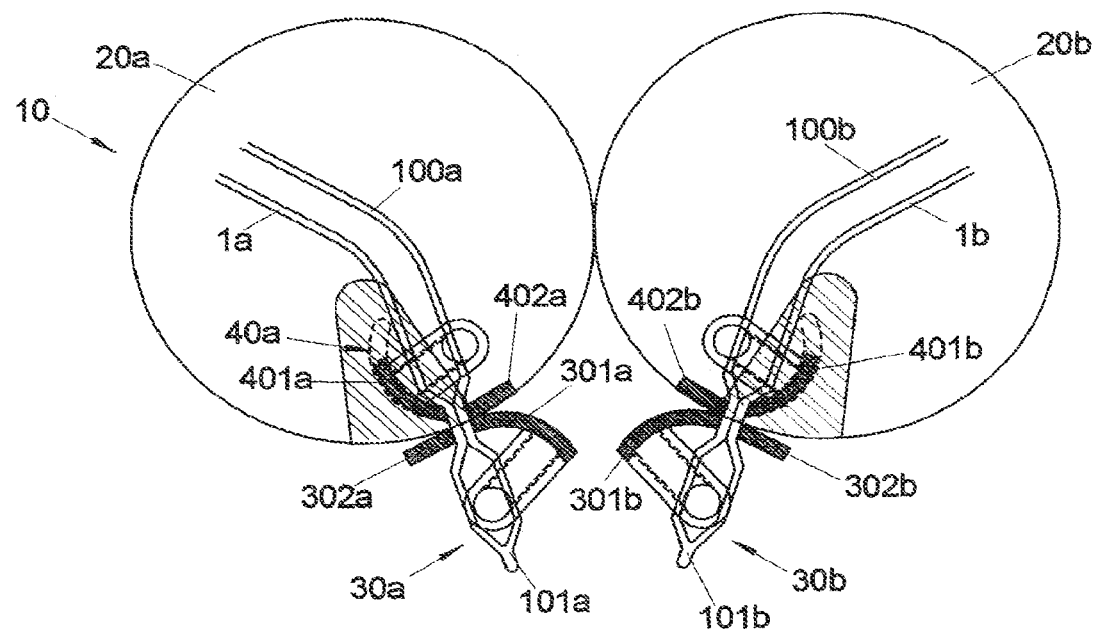
Figure 4D:
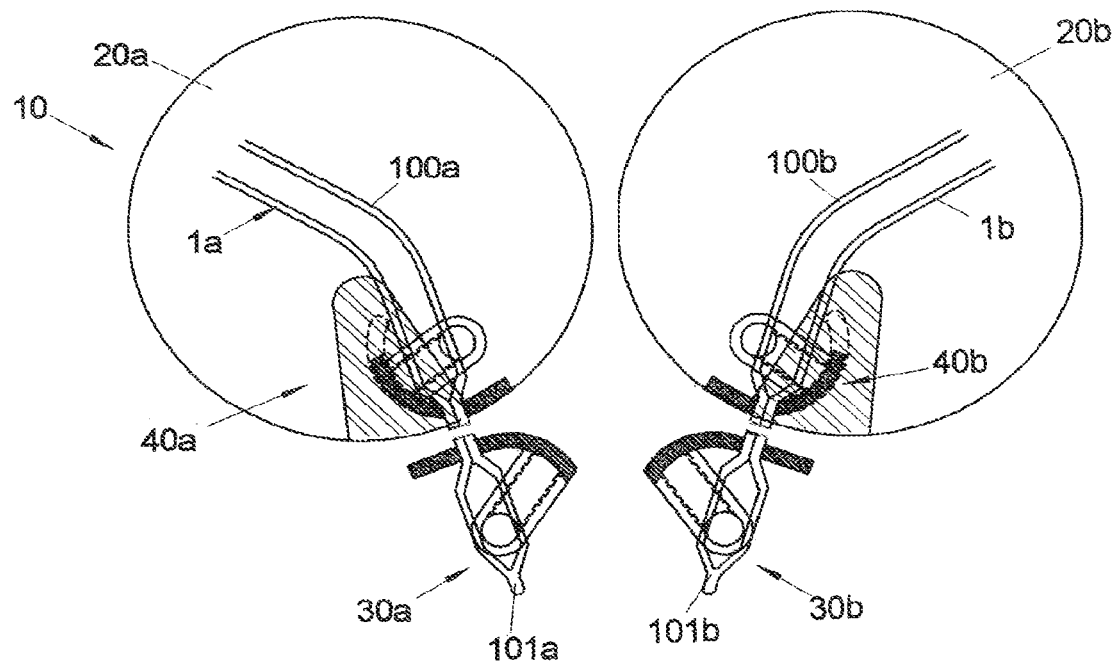
Figure 4E:
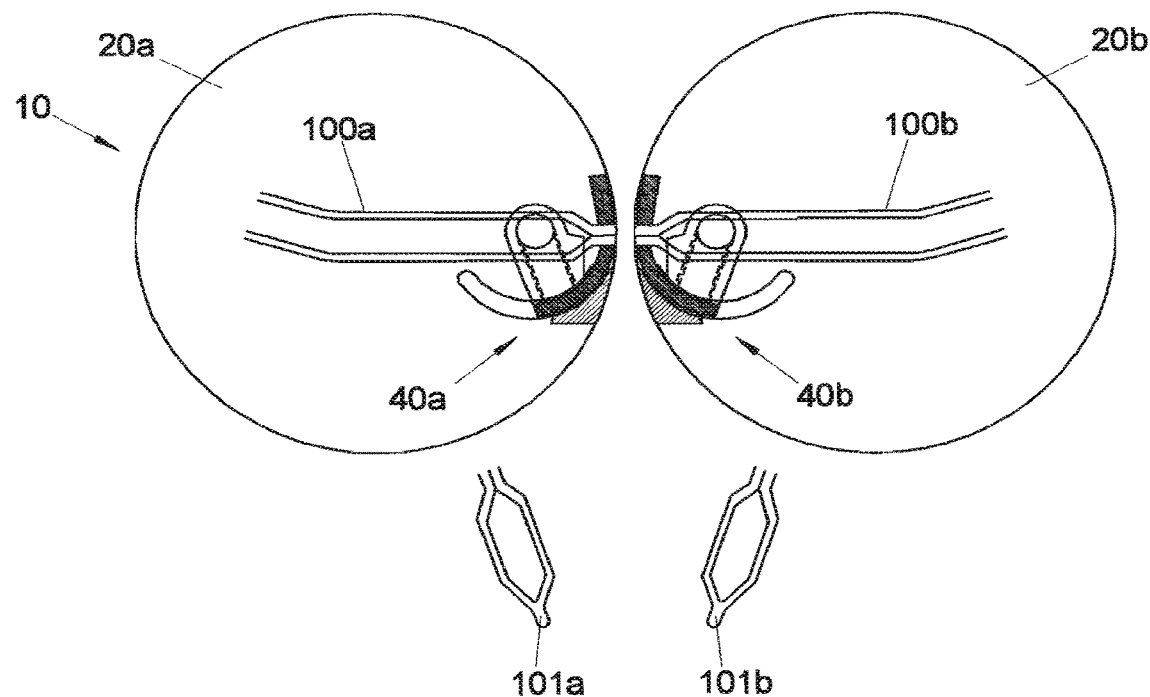
Figure 4F:
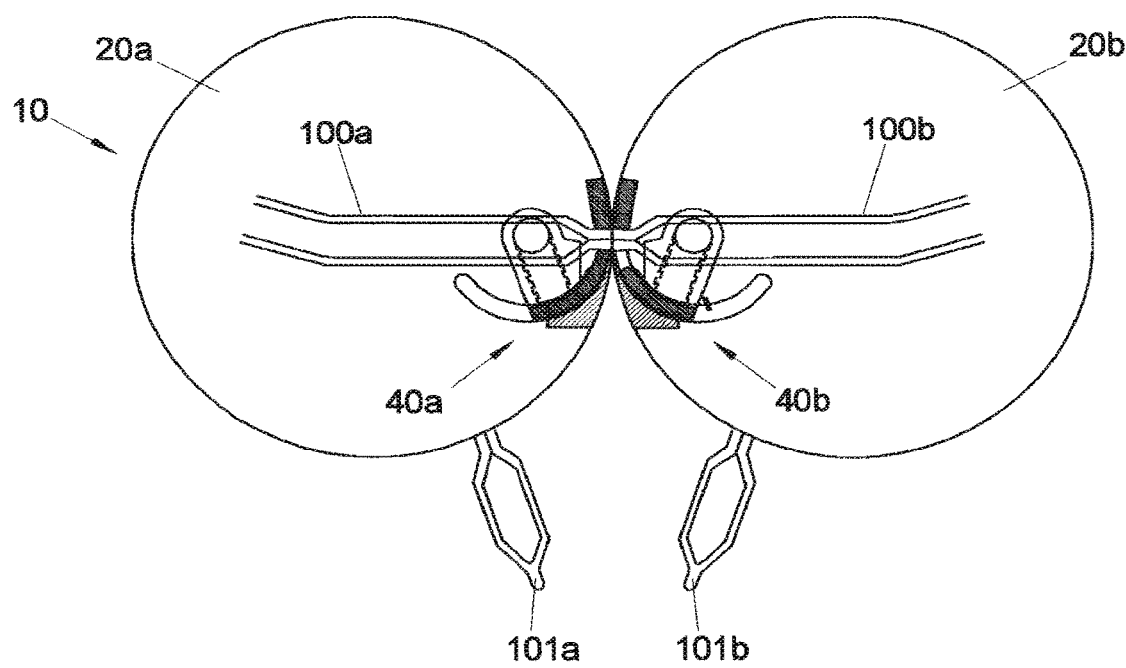
Figure 4G:
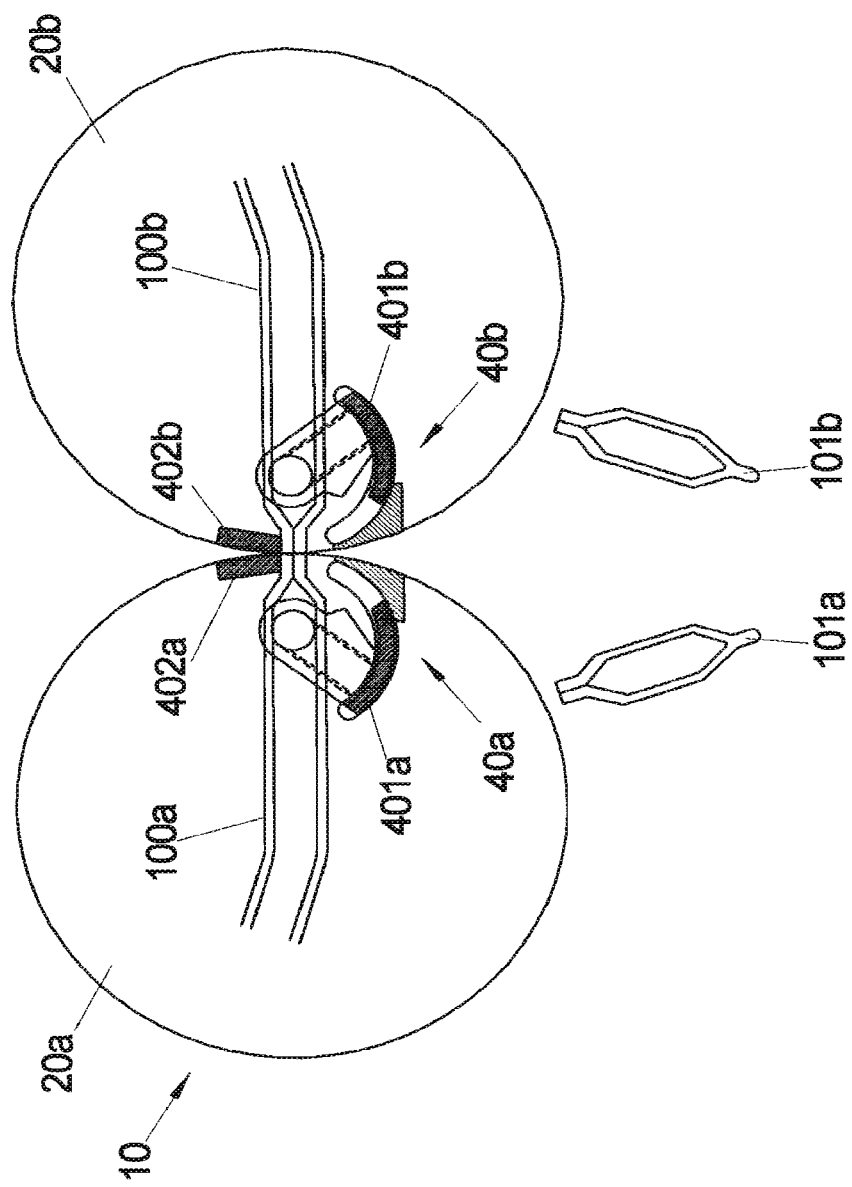
Figure 5A:
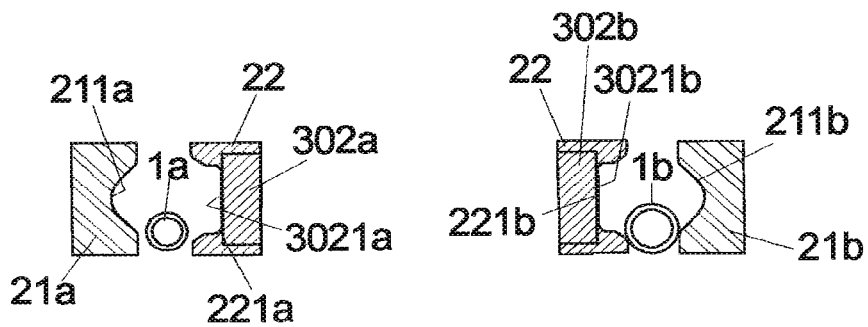
FIGS. 5A-5E show steps when centering tubes of different diameter arranged on a receiving device of the device according to the invention.
Figure 5B:
Figure 5C:
Figure 5D:
Figure 5E:

FIG. 4G shows the release of the tube, not illustrated in FIGS. 2A to 2H, after connection of the first tube portions, wherein the clamping jaws 401a, 401b of the second clamping device are removed from the tube, in particular after a cooling period, so that said tube can be removed from the device.

FIGS. 5A to 5E show in detail the centering of the tubes 1a, 1b implemented by the shape of the grooves 211a, 211b in the receiving bodies 40a, 40b and the guide body 22, wherein the tube 1a has a smaller diameter than the tube 1b.

The centering of the two tubes ensures that the midpoints of the tube cross sections are located at least approximately over the common longitudinal axis of the regions of the main tube portions 100a, 100b extending along this longitudinal axis after the separation of the tubes 1a, 1b and the alignment of the ends of the main tube portions 100a, 100b (for example see FIG. 2G discussed above). Tubes of different diameter can thus also be interconnected with the greatest possible connection quality. Another embodiment of the grooves in the receiving bodies 40a, 40b or the guide body 22 is shown in FIGS. 7A to 7F.

Figure 6A:
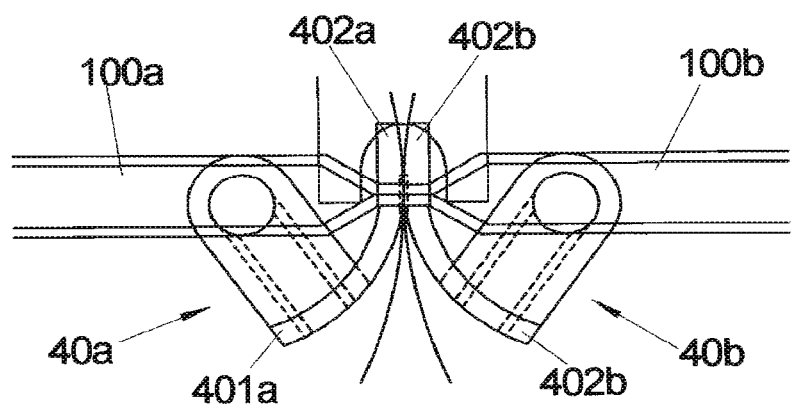
FIGS. 6A-6F show the positioning of first tube portions.
Figure 6B:
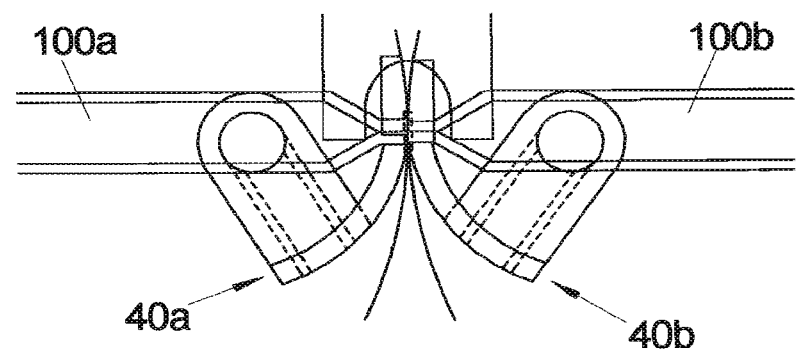
Figure 6C:
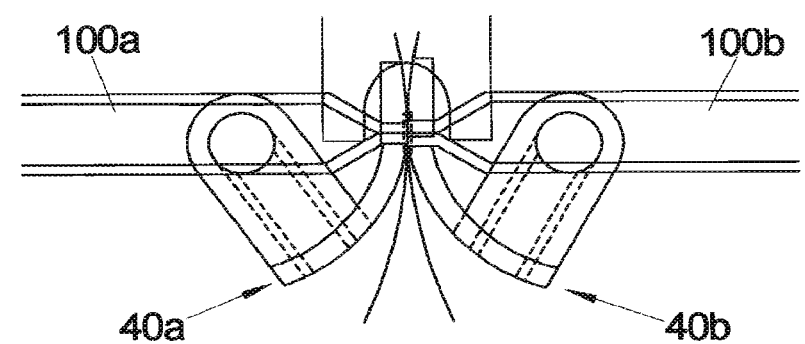
Figure 6D:
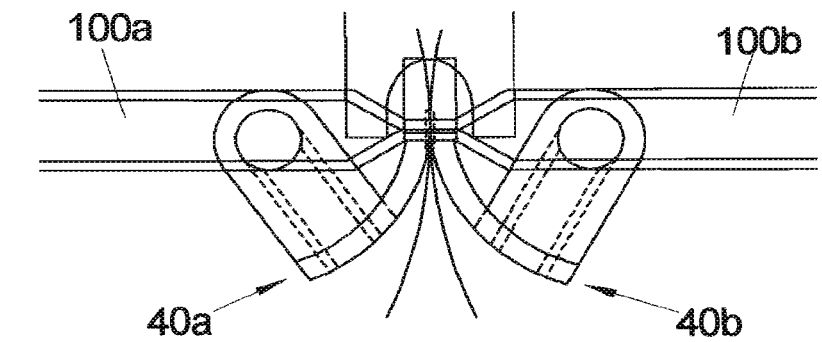

FIGS. 6A to 6D show the situation after production of the mechanical contact (analogously to FIG. 2H) between the ends of the main tube portions 100a, 100b, wherein different diameters of the interconnected main tube portions 100a, 100b are considered. In accordance with FIG. 6A, the two main tube portions 100a, 100b have the same diameter, and therefore their end faces lie practically completely against one another after production of the mechanical contact. FIG. 6D considers a similar case, wherein the two main tube portions 100a, 100b have a greater wall thickness however.

In accordance with FIG. 6B, one tube portion 100a has a greater diameter than the other main tube portion 100b, whereas the situation is reversed in FIG. 6C.

In both cases however, there is no offset between the main tube portion ends as a result of the centering mechanism illustrated with reference to FIGS. 5A to 5E, and therefore tubes of different diameter can also be reliably interconnected.

Figure 6E:
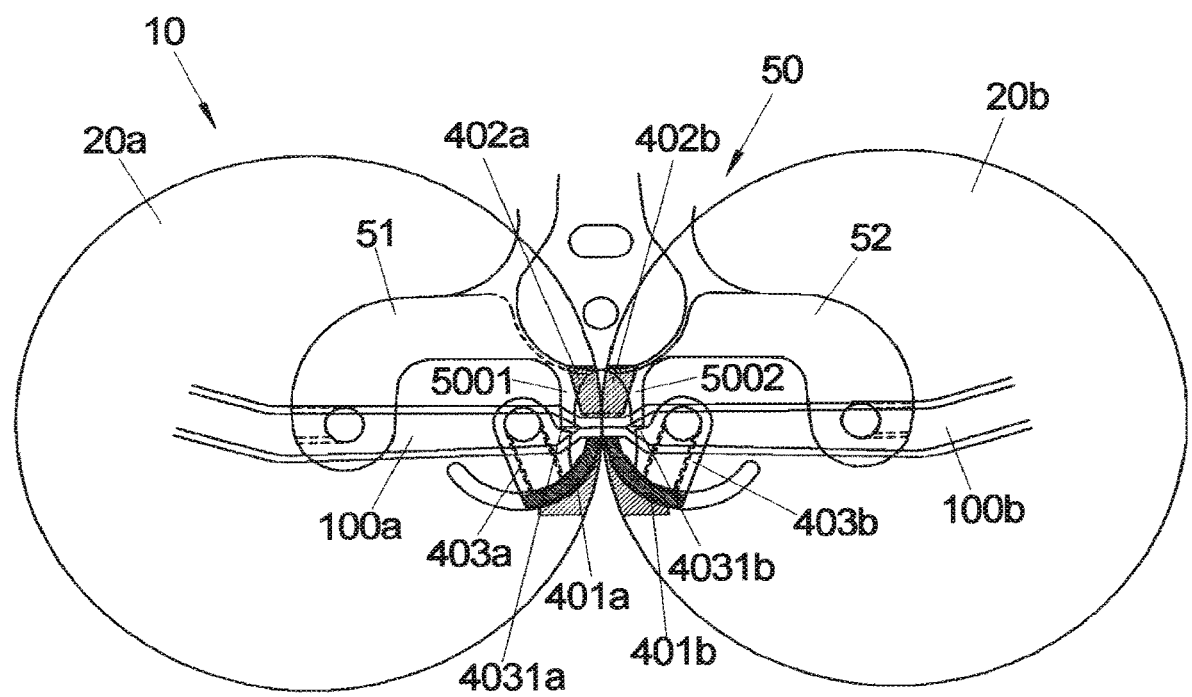
Figure 6E:
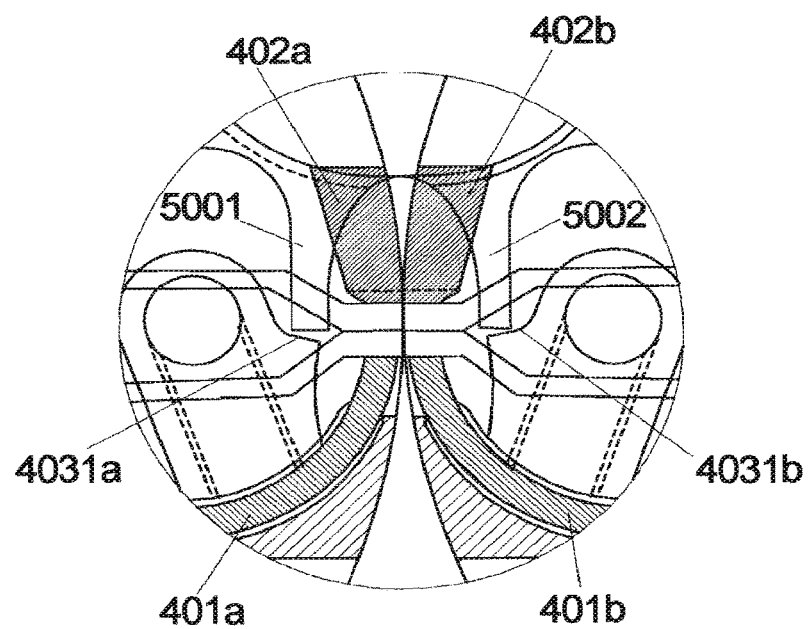
Figure 6F:
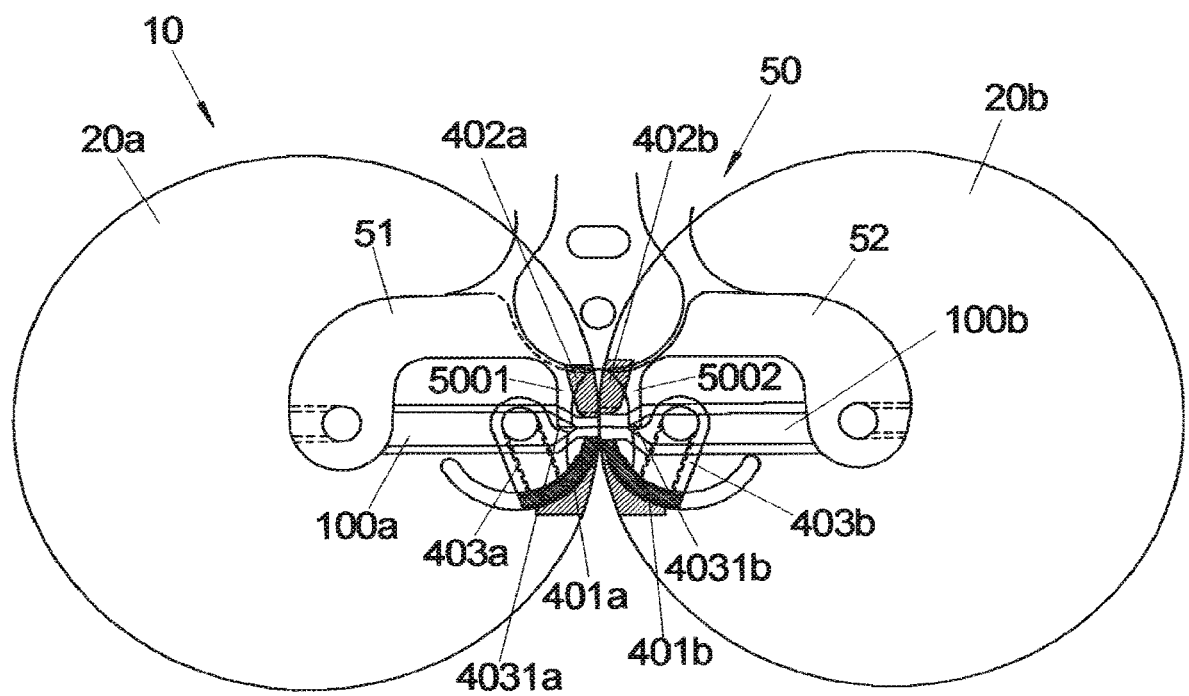
Figure 6F:
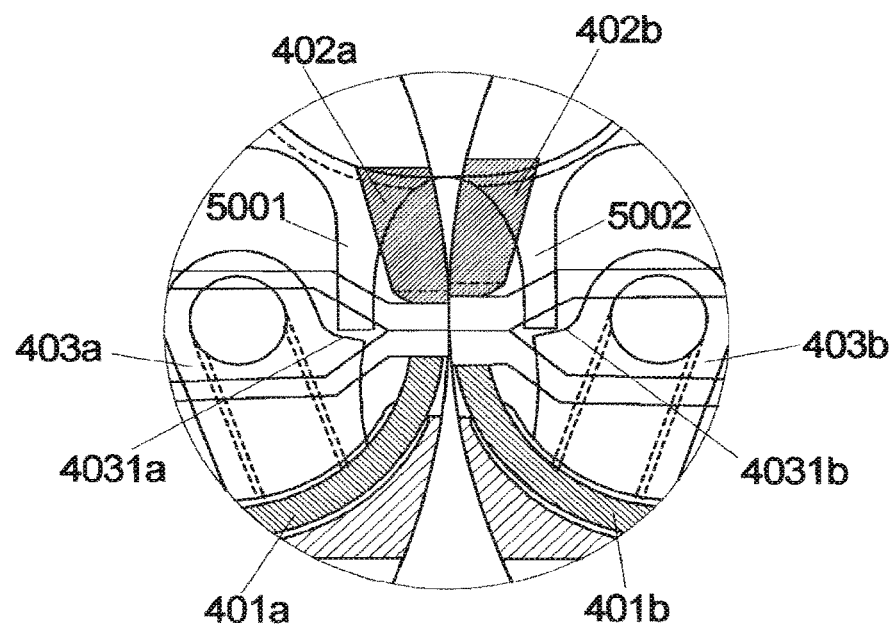

FIGS. 6E and 6F relate to a possibility, as a result of rotation of the disks 20a, 20b, of bringing first tube portions of different thickness as reproducibly as possible into a position in which their ends are arranged opposite one another along a common longitudinal axis. Analogously to FIGS. 3A to 3F, the device 10 accordingly comprises movement generation means 50 in the form of a pair of scissors, of which merely a lower region is shown in FIGS. 6E and 6F, that is to say in particular a lower portion of the arms 51, 52.

The arms 51, 52 of the movement generation means 50 each form a stop in the form of a protrusion 5001, 5002, which cooperate with arms 403a, 403b, via which the clamping jaws 401a, 401b can be rotated and which are arranged on the same side of the disks 20a, 20b as the arms 51, 52.

The arms 403a, 403b are connected to the clamping jaws 401a, 401b via a recess in the respective disk 20a, 20b.

The arms 403a, 403b each form a contact face 4031a, 4031b, wherein the disks 20a, 20b are rotated, so as to align the tube portions 100a, 100b along a common longitudinal axis, until the contact faces 4031a, 4031b come to bear against the protrusions 5001, 5002. A defined rotation of the disks 20a, 20b is thus enabled by means of the protrusions 5001, 5002, in such a way that the tube portions are each brought into a position, irrespective of their diameter, in which the axes of their ends are aligned; in particular see the enlarged detail in FIG. 6F shown beneath the primary illustration, in accordance with which two tube portions of different diameters are positioned such that their central axes are aligned. FIG. 6E relates to the case in which the two tube portions have the same diameter.

FIGS. 7A to 7F also relate to an embodiment of clamping devices, with which the tubes can be centered before separation. The principle of the centering process has already been explained with reference to FIGS. 5A to 5E. Clamping devices of this type can be implemented for example in the exemplary embodiment in FIGS. 2A to 2H.

Figure 7A:
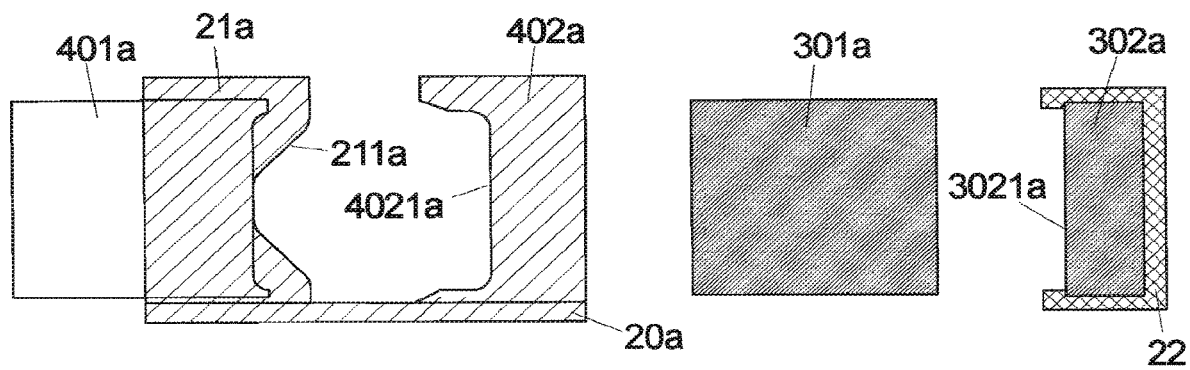
FIGS. 7A-7F show a first embodiment of clamping devices of the device according to the invention.
Figure 7B:
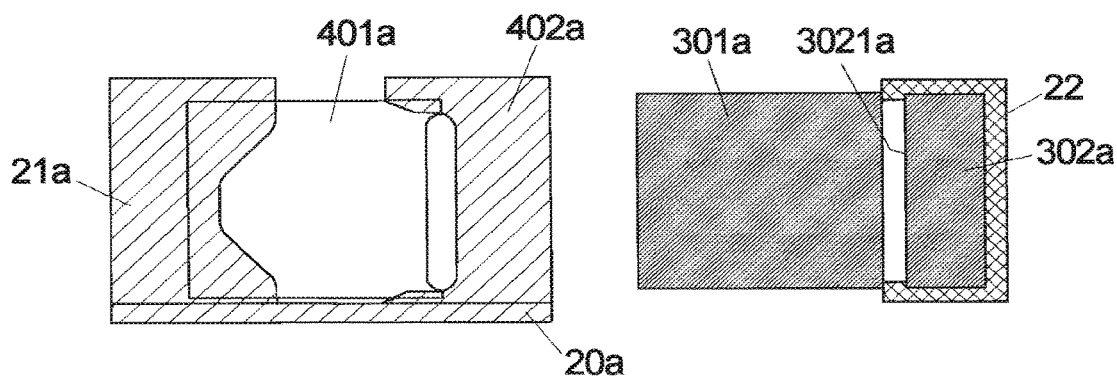
Figure 7C:
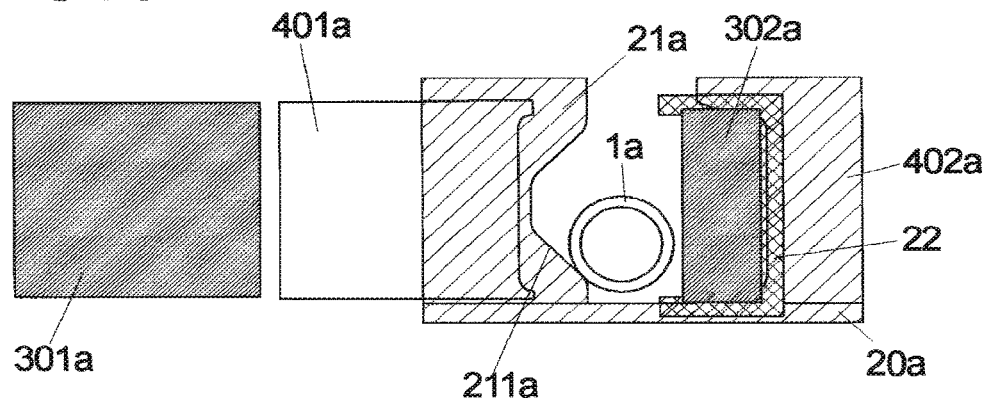
Figure 7D:
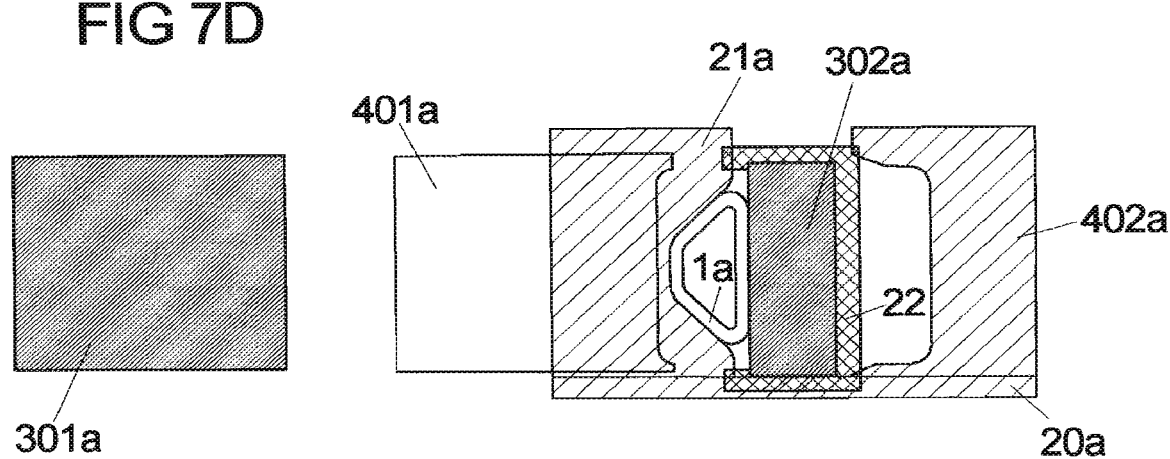

FIGS. 7A and 7B show the basic embodiment of the clamping devices, whereas FIGS. 7C to 7F illustrate steps during the clamping of a tube by means of the clamping devices.

In accordance with FIG. 7A, a first clamping device is provided with a first rotatable clamping jaw 301a and a second clamping jaw 302a (which is simultaneously a "hot" HF electrode, as described above), which is arranged in a guide body 22 (in particular an insulating guide body), analogously to FIG. 2A. A receiving body 21a with a groove 211a for guiding a tube as well as a second clamping device is also fixed to a receiving device (disk 20a), wherein the second clamping device comprises a first rotatable clamping jaw 401a and a second clamping jaw 402a arranged together with the receiving body 21a on the disk 20a.

FIG. 7A shows the clamping devices in the starting position, whereas FIG. 7B shows the clamping devices after rotation of the clamping jaws 301a and 401a. The clamping devices shown in FIGS. 7A to 7F correspond in particular to the left-hand side of the device 10 from FIG. 2A, that is to say they are each assigned to the disk 20a. The clamping devices on the right-hand side in FIG. 2A (that is to say the second disk 20b of the device 10) may comprise analogous clamping devices however.

To clamp a tube 1a, in the starting position of the clamping devices (FIG. 7C, analogously to FIG. 2A) said tube is positioned in particular between the groove 211a in the receiving body 21a and the clamping jaw 402a. The disk 20a is then rotated such that the tube 1a is pressed against the groove 211a and the clamping side 3021a of the clamping jaw 302a; see FIG. 7D (corresponding to FIG. 2B). The tube 1a is centered due to the V-shaped design of the groove 211a and a likewise U-shaped or V-shaped clamping side 4021a of the clamping jaw 402a.

Figure 7E:
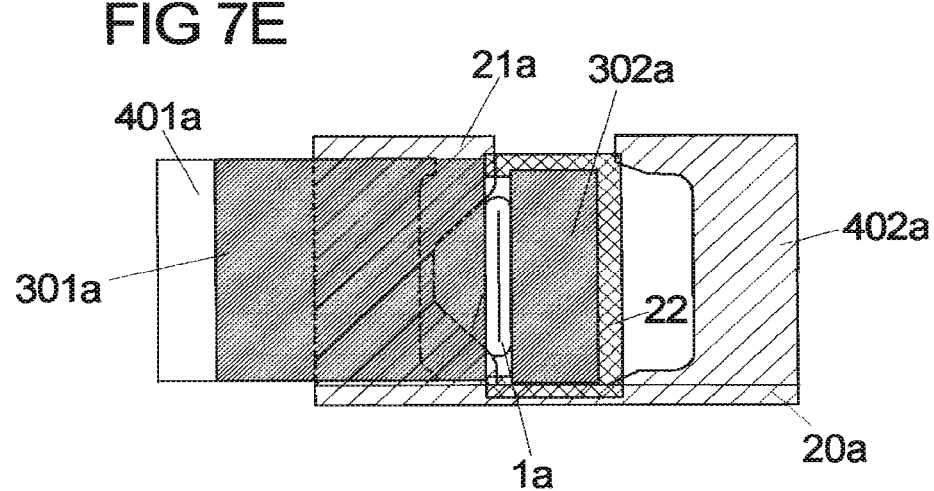
Figure 7F:
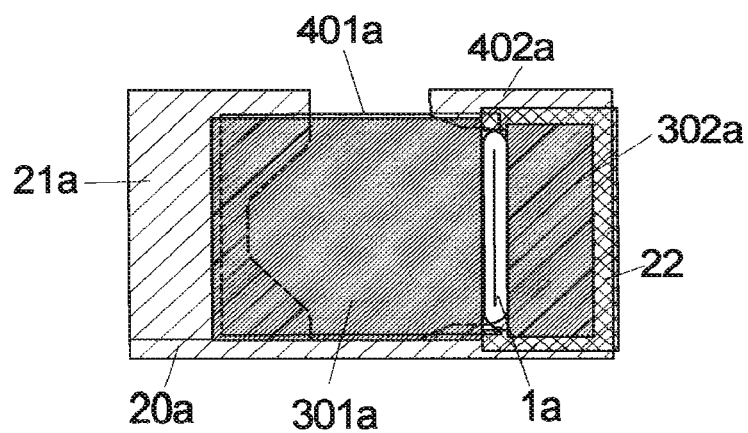

The clamping jaw 301a is then rotated such that the tube 1a is pressed together between the clamping jaws 301a and 302a, as illustrated in FIG. 7E (see FIG. 2C). The disk 20a is then rotated back in the direction of its starting position and the clamping jaw 401a is pivoted such that the tube 1a is clamped both between the clamping jaws 301a and 302a and between the clamping jaws 401a, 402a (FIG. 7F, corresponding to FIG. 2D).

FIGS. 8A to 8F show a modification of the clamping devices illustrated in FIGS. 7A to 7F, which in particular can be implemented in a device according to the exemplary embodiment in FIGS. 4A to 4G.

Analogously to FIGS. 7A and 7B, FIGS. 8A and 8B show the basic embodiment of the clamping devices, whereas FIGS. 8C to 8F illustrate steps during the clamping of a tube by means of the clamping devices.

Similarly to FIGS. 7A to 7F, FIGS. 8A to 8F concern clamping devices that are assigned to a disk 20a of the device. The clamping devices of the other disk 20b can be formed analogously however.

Figure 8A:
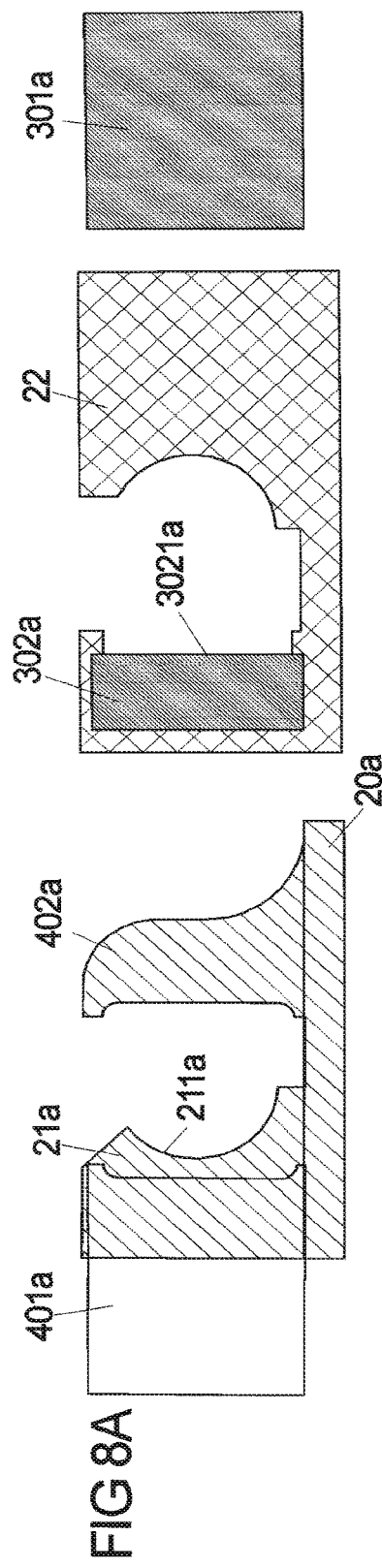
FIGS. 8A-8F show a second embodiment of clamping devices of the device according to the invention.
Figure 8B:
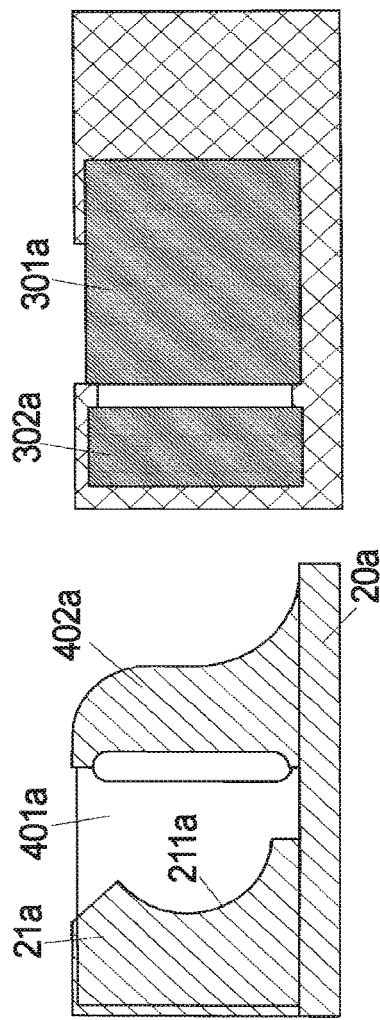
Figure 8C:
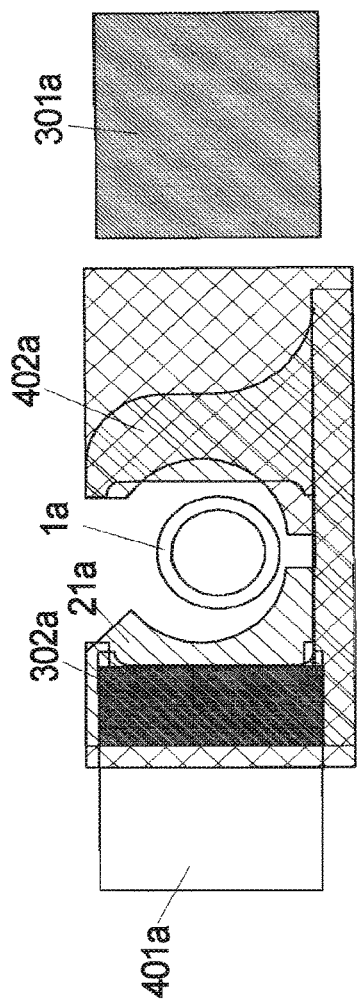
Figure 8D:
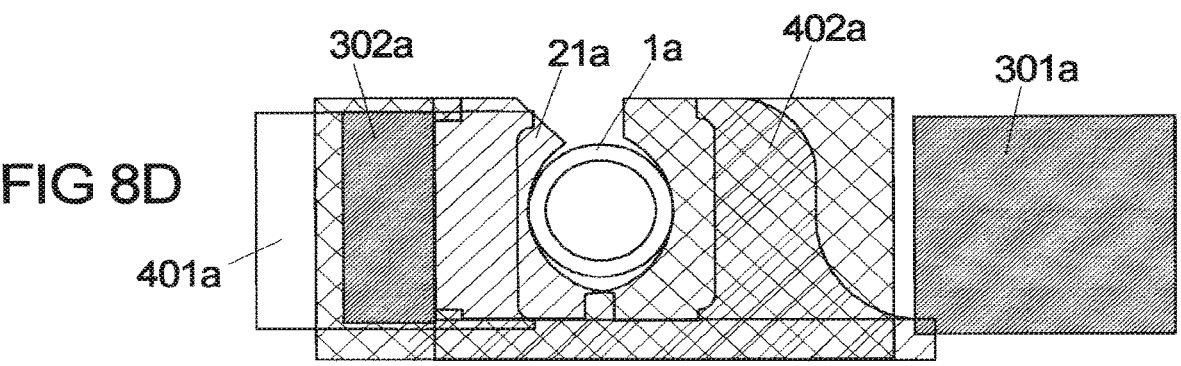
Figure 8E:
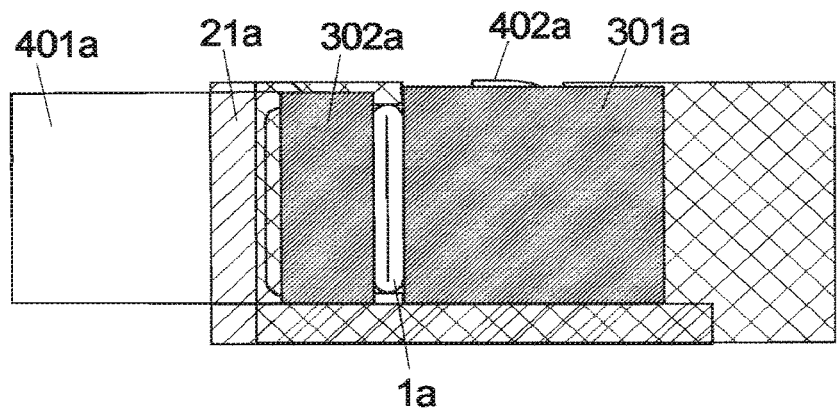
Figure 8F:
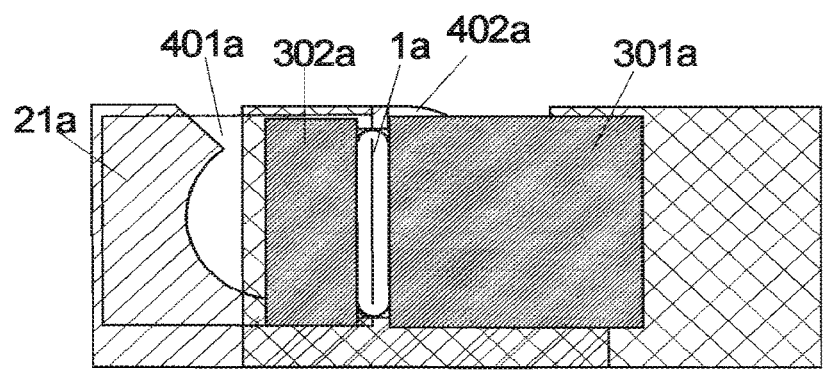

In contrast to FIGS. 7A to 7F, the clamping jaws 301a and 302a are "swapped", that is to say they are located on the respective other side of the tube to be clamped, which is why the guide body 22 is designed differently and, for example, engages around the tube on one side; see FIG. 8A. Furthermore, the groove 211a in the receiving body 21a is formed slightly differently, more specifically with a cross section that is at least approximately partly circular. At the same time, the clamping side 4021a of the clamping jaw 402a runs more flatly, for example is planar at least opposite the groove 211a. The positions of the clamping jaws and of the disk 20a illustrated in FIGS. 8C to 8F correspond to the positions of the clamping jaws in FIGS. 7C to 7F.

FIGS. 9A to 9F and FIGS. 10A to 10F show a third embodiment of clamping devices. FIGS. 9A to 9F show the clamping process for a tube having a first, relatively large diameter, whereas FIGS. 10A to 10F show the clamping process for a tube having a second diameter that is small relative to the first diameter.

In this embodiment the clamping jaws are formed in such a way that tubes of relatively large diameters are also grasped reliably over their entire periphery. This is achieved since the first clamping jaw 402a and the second clamping jaw 302a are cut out more deeply at the inner sides so as to better receive the tube. Tubes of large diameter are thus also reliably held between the clamping jaws, and the risk that the tubes will be pressed out in the edge region when clamped together between the clamping jaws can thus be minimized or prevented completely.

In accordance with a further embodiment, the device for the sterile connection of tubes is adapted in such a way that, for the purposes of ascertaining the welding parameters for the welding of the tubes, it carries out a pre-welding process and then carries out a further welding process in accordance with the parameter(s) ascertained. This makes it possible to weld together tubes having different properties, in particular of different diameters or wall thicknesses, or to take into account different conditions or states at the two clamping devices 30a, 30b, 40a, 40b.

The inserted tubes 1a, 1b (see FIG. 4A) are initially clamped with a defined force. Thick tubes are in this case clamped with a greater force compared to thinner tubes. In the event of subsequent connection of the ends of the two tubes, it is advantageous in this case that the two tubes have the same or at least approximate dimensions in the region of their tube ends so that the tube ends can thus be pressed against one another in a sufficiently matching manner. The clamping of larger tubes with a greater force also prevents the disadvantage that the oscillating circuit generating the high frequency no longer has to be sufficiently adjusted, which means that the thicker tube can no longer be heated as effectively.

The high frequency is then switched on for both tubes 1a, 1b. Once the tube has liquefied in the clamping portions as a result of the high frequency, the high frequency for the respective tube is switched off. The time between the switching on of the high frequency until liquefaction of the tube is measured for the respective tube 1a, 1b. In this case the degree of liquefaction of the tube is measured in each case via an encoder, which is connected to the motor and with which a displacement of the clamping jaws 301a, 301b of the first clamping devices 30a, 30b driven by the motor can be measured. As a result of the liquefaction, the clamping jaws 301a, 301b can be moved further toward one another than in the non-liquefied starting state. Once the clamping jaws have been moved toward one another by a specific distance (for example by a defined percentage, for example by a value in the range from 20% to 30%), it is possible to establish a specific degree of liquefaction. In addition, the force with which the clamping jaws clamp together the respective tube 1a, 1b can be taken into account via the measurement of the motor current.

The clamping jaws 401a, 402a and 401b, 402b of the second clamping devices then open at least in part and the second clamping devices are moved away slightly from the first clamping devices 302a, 301a and 301b, 302b, similarly to FIG. 4D but without separating the respective tube, wherein the respective tube is held however by the first clamping devices 30a, 30b and also is not separated. The second clamping devices 40a, 40b then again engage the respective tube, the first clamping devices 30a, 30b open at least in part, and the second clamping devices 40a, 40b are moved toward the first clamping devices 30a, 30b such that the respective tube is slid through the first clamping devices 30a, 30b over a short distance, generally a few millimeters, in the direction of the first clamping devices 30a, 30b until the weld points produced by the first welding process are driven out from the region of the first clamping devices 30a, 30b and a state similar to that shown in FIG. 4C is again achieved. The welding process then takes place with the learned parameters. In this case, the longer of the welding processes is started first so that both welding processes are concluded practically at the same time or preferably at the same time. The degree of liquefaction of the tube ends necessary for the subsequent connection of the two tube portions 100a and 100b is thus also achieved sufficiently, precisely at the same moment in time, for different tubes 1a, 1b.

Alternatively, it is likewise possible to regulate the welding process for the respective tubes 1a, 1b so that sufficient liquefaction is concluded at the same time or practically at the same time. The regulation can be implemented by readjusting the intensity of the high frequency in accordance with the displacement of the clamping jaws. With regulation of this type, it is possible to dispense with the step of "pre-welding" as described above.

The motors that drive the clamping jaws 401a, 402a of the second clamping devices 40a, 40b may also be equipped with encoders. This makes it possible, for example with consideration of the motor current, to identify whether the tubes 1a, 1b have been grasped correctly by the respective second clamping device.

It is noted that elements in the above figures may of course in principle be used in any combination with one another. For example, the movement generation means in FIGS. 3A to 3F can be used together with the embodiment of the device according to FIGS. 4A to 4G. It is also conceivable for example that differently designed clamping jaws are used; for example clamping jaws according to FIGS. 7A to 7F are assigned to the first disk 20a and clamping jaws according to FIGS. 8A to 8F are assigned to the second disk.

LIST OF REFERENCE SIGNS 1a, 1b tube
20a, 20b rotatable disk
21a, 21b receiving body
22 guide body
30a, 30b first clamping device
40a, 40b second clamping device
50 movement generation means
51 first arm
52 second arm
53 center of rotation
55 annular disk
56, 57 connection elements
100a, 100b first tube portion
101a, 101b second tube portion
211a, 211b groove
221a, 221b groove
301a, 301b first clamping jaw first clamping device
302a, 302b second clamping jaw first clamping device
303a, 303b, 403a, 403b arm
305a clamping face first clamping jaw
306a clamping face second clamping jaw
401a, 401b first clamping jaw second clamping device
402a, 402b second clamping jaw second clamping device
403a, 403b arm
511, 521 connection means
512, 513 upper end
514, 515 lower end
1001a, 1001b end of the first tube portion
3021a, 3021b clamping side
4021a clamping side
4031a, 4031b contact face
5001, 5002 protrusion

The invention claimed is:

1. A method of making and opening a sterile connection between ends of two thermoplastic tubing segments comprising:
heating the ends of each segment to a temperature above the melting point of the thermoplastic material;
moving both of the heated ends of the tubing segments into face to face contact and allowing material of the ends to fuse together to form a head-bonded connection between the tubing segments, which connection includes a closure of thermoplastic material, formed during the heat-bonding closing flow between the tubing segments; and
applying external pressure to the connection site to open the closure to allow flow between the tubing segments.

2. The method of claim 1 including applying external pressure until the closure is opened.

3. The method of claim 2 including determining if the correct tubing segments are connected before applying pressure to the connection site to open the closure.

4. The method of claim 1 in which light pressure is applied to the connection site.

5. A method of making and opening a sterile connection between ends of two thermoplastic tubing segments comprising:
heating the ends of each segment to a temperature above the melting point of the thermoplastic material;
bringing the heated ends of the tubing segments into face to face contact and allowing material of the ends to fuse together to form a head-bonded connection between the tubing segments, which connection includes a closure of thermoplastic material, formed during the heat-bonding closing flow between the tubing segments; and
applying external pressure to the connection site to open the closure to allow flow between the tubing segments, wherein the pressure is manually applied.

6. The method of claim 5 including applying external pressure until the closure is opened.

7. The method of claim 6 including determining if the correct tubing segments are connected before applying pressure to the connection site to open the closure.

8. The method of claim 5 in which light pressure is applied to the connection site.

9. The method of claim 5 in which bringing the heated ends of the tubing into face to face contact includes moving both of the heated ends.

10. The method of claim 1 in which heat is not applied during the time that the ends are fused together.

11. The method of claim 1 wherein the ends are moved away from a heat source during the time that the ends are fused together.

12. The method of claim 1 in which the tubing segments have different diameters.

13. The method of claim 2 in which determining if the correct tubing segments are connected includes scanning labels associated with each of the two tubing segments.

14. The method of claim 1 in which heating the ends of each segment includes each tubing segment being clamped shut with a first clamping device and a second clamping device.

15. The method of claim 14 in which moving both of the heated ends of the tubing segments into face to face contact includes separating each tubing segment into a first tube portion and a second tube portion, with the time between the separation of each of the tubing segments into the first and second tube portions to the time of face to face contact being no more than 0.1 second.

16. The method of claim 5 in which heat is not applied during the time that the ends are fused together.

17. The method of claim 5 in which the tubing segments have different diameters.

18. The method of claim 5 in which the ends are moved away from a heat source during the time that the ends are fused together.

19. The method of claim 5 in which heating the ends of each segment includes each tubing segment being clamped shut with a first clamping device and a second clamping device.

20. The method of claim 19 in which bringing the heated ends of the tubing segments into face to face contact includes separating each tubing segment into a first tube portion and a second tube portion, with the time between the separation of each of the tubing segments into the first and second tube portions to the time of face to face contact being no more than 0.1 second.

\* \* \* \* \*